US011382885B2

(12) United States Patent
Nobile et al.

(10) Patent No.: US 11,382,885 B2
(45) Date of Patent: *Jul. 12, 2022

(54) COMPOSITIONS FOR TREATING FUNGAL AND BACTERIAL BIOFILMS AND METHODS OF USING THE SAME

(71) Applicant: The Regents of the University of California, Oakland, CA (US)

(72) Inventors: Clarissa J. Nobile, Merced, CA (US); Megha Gulati, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/620,124

(22) PCT Filed: Jun. 7, 2018

(86) PCT No.: PCT/US2018/036501
§ 371 (c)(1),
(2) Date: Dec. 6, 2019

(87) PCT Pub. No.: WO2018/226987
PCT Pub. Date: Dec. 13, 2018

(65) Prior Publication Data
US 2020/0222349 A1 Jul. 16, 2020

Related U.S. Application Data

(60) Provisional application No. 62/516,587, filed on Jun. 7, 2017.

(51) Int. Cl.
| *A61K 31/198* | (2006.01) |
| *A61P 31/04* | (2006.01) |
| *A61P 31/10* | (2006.01) |
| *A61K 31/133* | (2006.01) |
| *A61K 31/401* | (2006.01) |
| *A61K 31/405* | (2006.01) |
| *A61K 31/4172* | (2006.01) |
| *A61K 31/661* | (2006.01) |
| *A61K 47/08* | (2006.01) |

(52) U.S. Cl.
CPC .......... *A61K 31/198* (2013.01); *A61K 31/133* (2013.01); *A61K 31/401* (2013.01); *A61K 31/405* (2013.01); *A61K 31/4172* (2013.01); *A61K 31/661* (2013.01); *A61K 47/08* (2013.01); *A61P 31/04* (2018.01); *A61P 31/10* (2018.01)

(58) Field of Classification Search
CPC .. A61K 31/198; A61K 31/131; A61K 31/401; A61K 31/661; A61K 47/08; A61K 31/4172; A61K 31/405; A61K 31/133; A61P 31/04; A61P 31/10
See application file for complete search history.

(56) References Cited

U.S. PATENT DOCUMENTS

| 3,922,202 | A | 11/1975 | Hallada et al. |
| 4,826,680 | A | 5/1989 | Jaeger |
| 4,871,550 | A | 10/1989 | Millman |
| 5,112,810 | A | 5/1992 | Nagai et al. |
| 5,366,723 | A | 11/1994 | Tulok |
| 5,711,937 | A | 1/1998 | Nisiida et al. |
| 5,811,446 | A | 9/1998 | Thomas |
| 5,872,127 | A | 2/1999 | Cincotta et al. |
| 6,103,748 | A | 8/2000 | Bryan |
| 6,274,612 | B1 | 8/2001 | Bryan |
| 7,906,544 | B2 | 3/2011 | Melander et al. |
| 8,241,611 | B2 | 8/2012 | Dashper et al. |
| 8,420,673 | B2 | 4/2013 | Pasteris et al. |
| 8,425,932 | B2 | 4/2013 | Wryer et al. |
| 8,980,307 | B2 | 3/2015 | Harris et al. |
| 9,370,486 | B2 | 6/2016 | Chen |
| 9,480,669 | B2 | 11/2016 | Bryan et al. |
| 9,549,904 | B2 | 1/2017 | Bryan |
| 9,732,164 | B2 | 8/2017 | Baker et al. |
| 2004/0033959 | A1 | 2/2004 | Chen et al. |
| 2005/0064014 | A1 | 3/2005 | Finot et al. |
| 2011/0046041 | A1 | 2/2011 | Neesham-Grenon et al. |
| 2011/0236453 | A1 | 9/2011 | Stensen et al. |
| 2012/0004157 | A1 | 1/2012 | Aksnes |
| 2012/0315260 | A1 | 12/2012 | Ivanova et al. |
| 2013/0059096 | A1 | 3/2013 | Losick et al. |
| 2013/0123319 | A1 | 5/2013 | Bryan |
| 2014/0018438 | A1 | 1/2014 | Bryan |

(Continued)

FOREIGN PATENT DOCUMENTS

| GB | 2 514 863 A | 12/2014 |
| WO | WO-99/65479 A1 | 12/1999 |

(Continued)

OTHER PUBLICATIONS

Vale et al., "Amino Acids in the Development of Prodrugs", 2018, Molecules, 23(9), pp. 1-61. (doi:10.3390/molecules23092318) (Year: 2018).*

Edited by Rowe et al., (2009), "Handbook of Pharmaceutical Excipients (6th ed.)", London: APhA, (PhP) Pharmaceutical Press., pp. 637-640. (Year: 2009).*

Abd, M. et al. (2014). "N-acetylcysteine Inhibits and Eradicates Candida albicans Biofilms," *American J. Infectious Diseases and Microbiology* 2(5):122-130.

(Continued)

*Primary Examiner* — My-Chau T. Tran
(74) *Attorney, Agent, or Firm* — Mintz, Levin, Cohn, Ferris, Glovsky and Popeo, P.C.

(57) ABSTRACT

The disclosure provides compositions comprising amino acids, individually and in combination, and methods of making the compositions and methods of using the compositions as pharmaceutically active agents to, inter *alia*, treat disease in animals, including humans.

20 Claims, No Drawings

(56) References Cited

U.S. PATENT DOCUMENTS

| | | |
|---|---|---|
| 2014/0056951 A1 | 2/2014 | Losick et al. |
| 2015/0126571 A1 | 1/2015 | Bryan |
| 2017/0042851 A1 | 2/2017 | Bryan et al. |
| 2018/0153840 A1 | 6/2018 | Bryan |
| 2018/0214411 A1* | 8/2018 | Vetter .................... A61K 47/14 |

FOREIGN PATENT DOCUMENTS

| | | |
|---|---|---|
| WO | WO-2011/085326 A1 | 7/2011 |
| WO | WO-2011/085326 A9 | 7/2011 |
| WO | WO-2016/112140 A1 | 7/2016 |
| WO | WO-2018/042367 A2 | 3/2018 |
| WO | WO-2018/042367 A3 | 3/2018 |
| WO | WO-2020/117755 A1 | 6/2020 |

OTHER PUBLICATIONS

Drugs & Medications—Amino Acids-E-lyte-Glycerin IV; http://www.webmd.com/drugs/drug-63311-Amino+Acids-E-lyte-Glycerin+IV_aspx?drugid=63311&drugname=Amino+Acids-E-lyte-Glycerin+IV.

Fitzpatrick, F. et al. (Apr. 2005). "Evidence for icaADBC-independent biofilm development mechanism in methicillin-resistant *Staphylococcus aureus* clinical isolates," *J Clin Microbiol* 43(4):1973-1976.

Helms, S. et al. (2006). "Natural Treatment of Chronic Rhinosinusitis," *Alternative Medicine Review* 11(3):196-207.

International Search Report dated May 6, 2016, for PCT Application No. PCT/US2016/012395, filed Jan. 6, 2016, 4 pages.

International Search Report dated Aug. 28, 2018, for PCT Application No. PCT/US2018/036501, filed on Jun. 7, 2018, 4 pages.

International Search Report dated Feb. 10, 2020, for PCT Application No. PCT/US2019/064165, filed Dec. 3, 2019, 4 pages.

Percival, S.L. et al. (Jan.-Feb. 2008). "Assessing the effect of an antimicrobial wound dressing on biofilms," *Wound Repair Regen* 16(1):52-57.

Ponikau, J.U. et al. (Sep. 1999). "The diagnosis and incidence of allergic fungal sinusitis," *Mayo Clin Proc* 74(9):877-884.

Rona, Z. Naturally Savvy (2013). pp. 1-13.

Suh, J.D. et al. (Feb. 2010). "Biofilms in chronic rhinosinusitis," *Curr Opin Otolaryngol Head Neck Surg* 18(1):27-31.

Thomas, E.D. et al. (Sep. 12, 1957). "Intravenous Infusion Of Bone Marrow In Patients Receiving Radiation And Chemotherapy," *The New England Journal of Medicine* 257(11):491-496.

Kenner, D. (Oct. 2007). Treatment Of Infections Without Antibiotics, located at http://www.thenhf.com/old/articles/articles_594/articles_594.htm, 5 pages.

Tong, et al. (Jun. 2014). *PLoS One* 9(6):1-8.

Written Opinion dated May 6, 2016, for PCT Application No. PCT/US2016/012395, filed Jan. 6, 2016, 9 pages.

Written Opinion dated Aug. 28, 2018, for PCT Application No. PCT/US2018/036501, filed on Jun. 7, 2018, 15 pages.

Written Opinion dated Feb. 10, 2020, for PCT Application No. PCT/US2019/064165, filed Dec. 3, 2019, 9 pages.

* cited by examiner

COMPOSITIONS FOR TREATING FUNGAL AND BACTERIAL BIOFILMS AND METHODS OF USING THE SAME

CROSS-REFERENCE TO RELATED APPLICATIONS

This application is a Section 371 U.S. national phase of International Application No. PCT/US2018/036501 filed Jun. 7, 2018, which claims priority to U.S. Application No. 62/516,587 filed Jun. 7, 2017, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant nos. R00AI100896 and R35GM124594 awarded by the National Institutes of Health. The government has certain rights in the invention.

FIELD

The embodiments disclosed herein relate generally to compositions comprising amino acids, individually and in combination, and relate to methods of making the compositions and methods of using the compositions as pharmaceutically active agents to treat disease in animals, including humans.

BACKGROUND

Bacterial and fungal infections are a major cause of morbidity and mortality and there is an urgent need for the development of new antibacterial and antifungal agents. According to the CDC, 63% of bacterial pathogens that cause human disease produce biofilms. Candidiasis is the most common fungal infection and *Candida* spp. have become the fourth leading cause of bloodstream infections in the United States (Edmond et al., Clin Infect Dis, 29:239-244 (1999); Pfaller et al., Clin Microbiol Rev, 20:133-163 (2007)). In addition to the morbidity and mortality associated with systemic candidiasis, localized infections are also a significant health issue. *Candida* spp. are the second most common cause of urinary tract infection (Laupland et al., J Crit Care, 17:50-57 (2002)) and according to different studies, approximately 70% of women experience vaginal infections caused by *Candida* spp., 20% of them suffer from recurrent infections, and of these latter recurrent infections, about half of the patients have four or more episodes per year (Paulitsch et al., Mycoses, 49:471-475 (2006); Corsello et al., Eur J Obstet Gynecol Reprod Biol, 110:66-72 (2003); Ventolini et al., J Reprod Med, 51:475-478 (2006)). The success of bacteria in producing resistance to known antibiotics is most likely due to their ability to produce biofilms which protects immature bacteria from the immune system and from antibiotics. The success of *Candida albicans* as a human pathogen is a result of their diverse armamentarium of virulence factors. *C. albicans* colonizes mucosal surfaces, such as the gastrointestinal tract (isolated from over half of the oral cavities of healthy adults) and vaginal epithelium (Paulitsch et al., Mycoses, 49:471-475 (2006); Kumamoto et al., Annu Rev Microbiol, 59:113-133 (2005); Li et al., Microbiology, 149:353-362 (2003)). *Candida* virulence is a result of its ability to form biofilms, switch between different forms, and produce filaments in response to environmental conditions (Berman et al., Nat Rev Genet, 3:918-932 (2002); Kobayashi et al., Trends Microbiol, 6:92-94 (1998)). *Candida* biofilm formation has important clinical repercussions because of their increased resistance to antifungal therapy and the ability of cells within biofilms to withstand host immune defenses, resulting in treatment failure and the need to remove catheters and other biological materials (Kumamoto et al., Annu Rev Microbiol, 59:113-133 (2005); Kojic et al., Clin Microbiol Rev, 17:255-267 (2004); Raad, Middle East J Anesthesiol, 12:381-403 (1994); Ramage et al., FEMS Yeast Res, 6:979-986 (2006); Richard et al., Eukaryot Cell, 4:1493-1502 (2005)).

Microbes that attach to surfaces aggregate in a hydrated polymeric matrix of their own synthesis to form biofilms. Formation of these sessile communities and their inherent resistance to antimicrobial agents are at the root of many persistent and chronic microbial bacterial infections. (*Science* 21 May 1999: Vol. 284, Issue 5418, pp. 1318-1322).

According to the center for disease control, 63% of treated bacterial infections develop a biofilms. Biofilms are implicated in chronic infections. Most notable among them is *Staphylococcus aureus*, especially the methicillin resistant (MRSA) variety. Also, an estimated 13% of intensive care patients have a fungal infection likely originating from a biofilm.

Virulence factors of both fungal and bacterial infections also create an environment conducive to formation of biofilms. While scientists have characterized some of the biological cues and secretion patterns of infections correlated with fungal and bacterial biofilms, chronic infections of both bacterial and fungal due to biofilms remain largely untreatable. There are no effective treatments for either fungal or bacterial biofilms that can treat or prevent the formation of biofilms within a subject, or on an implanted device in a patient or within a catheter that is in fluid communication with a subject.

SUMMARY OF EMBODIMENTS

Thirty-four amino acids that naturally occur in human serum were examined for their effect on bacterial and fungal biofilms (see Tables D and E).

The disclosure relates to pharmaceutical compositions comprising one or a plurality of non-bonded amino acids or pharmaceutically acceptable salts thereof for treatment of fungal and bacterial infections comprising one or a plurality of microorganisms in the form of a biofilm.

In some embodiments, the pharmaceutical compositions are free of the non-bonded L-amino acids: alanine, arginine, asparagine, citrulline, glycine, isoleucine, leucine, methionine, lysine, 3-methylhistadine, phenylanine, ornithine, proline, serine, and taurine, threonine, tryptophan, and/or valine.

The disclosure also relates to the compositions, pharmaceutical compositions or formulations disclosed herein for use in the prevention of bacterial and/or fungal biofilm formation. Also provided herein are the compositions, pharmaceutical compositions or formulations described herein for use in the treatment of a fungal infection or bacterial infection, and/or in the manufacture of a medicament for the treatment of a fungal infection and/or a bacterial infection. In some embodiments, the composition comprises non-bonded beta-alanine, or a pharmaceutically acceptable salt thereof, at a weight to volume percent from about 0.1% to about 5.0%; non-bonded 2-aminoadipic acid, or a pharmaceutically acceptable salt thereof, at a weight to volume percent from about 0.1% to about 5.0%; non-bonded aspartic acid, or a pharmaceutically acceptable salt thereof, at a weight to volume percent from about 0.1% to about 5.0%; non-bonded cystathionine (0.2%), or a pharmaceutically acceptable salt thereof, at a weight to volume percent from about 0.1% to about 5.0%; non-bonded cysteine, or a pharmaceutically acceptable salt thereof, at a weight to volume percent from about 0.1% to about 5.0%; non-bonded ethanolamine, or a pharmaceutically acceptable salt thereof, at a weight to volume percent from about 0.1% to about 5.0%; non-bonded glutamic acid, or a pharmaceutically acceptable salt thereof, at a weight to volume percent from about 0.1% to about 5.0%, non-bonded homocysteine, or a pharmaceutically acceptable salt thereof, at a weight to volume percent from about 0.1% to about 5.0%; non-bonded hydroxyproline, or a pharmaceutically acceptable salt thereof, at a weight to volume percent from about 0.1% to about 5.0%; non-bonded phosphoethanolamin, or a pharmaceutically acceptable salt thereof, at a weight to volume percent from about 0.1% to about 5.0%; non-bonded phosphoserine, or a pharmaceutically acceptable salt thereof, at a weight to volume percent from about 0.1% to about 5.0%.

The disclosure also relates to the compositions, pharmaceutical compositions or formulations disclosed herein for use in treatment of a surface for disinfecting purposes. In some embodiments, the surface is a surface of an implantable device or a catheter or drain tube. In some embodiments of the methods described herein, the fungal infection is infection with a *Candida* species fungus, e.g., *C. albicans*. In some embodiments, the bacterial infection is a bacterial infection caused by antibiotic-resistant bacteria. In some embodiments, the infection is a fungus which produces a biofilm. In some embodiments, the infection is a bacterium which produces a biofilm. In some embodiments, the bacterial cells that induce infection are one or a plurality of bacterial cells derived from or chosen from one or a plurality: *Streptococcus pneumoniae, Bacillus* spp, *Listeria monocytogenes, Staphylococcus* spp, and lactic acid bacteria, including *Lactobacillus plantarum* and *Lactococcus lactis*, and/or *Streptococcus mutans*.

TABLE A

| Indwelling Medical Device | Organisms |
| --- | --- |
| Central Venous Catheter | Coagulase-negative *staphylocci, Staphylococcus aerues, Enterococcus faecalis, Klebsiella pneumonia, Pseudomonas aeruginosa, Candida albicans* |
| Prosthetic Heart Valve | *Viridans Streptococcus*, coagulase-negative *staphylococci, enterococci, Staphylococcus aureus* |
| Urinary Catheter | *Staphyloccus epidermidis, Escherichia coli, Klebsiella pneumoniae, Enteroccus faecalis, Proteus mirabilis* |
| Artificila Hip Prosthesis | Coagulase-negative *staphylocci*, β-hemolytic *streptocci, enterocci, Proteus mirabilis, Bacteriodes species, Staphyloccus aureus, viridans Streptococcus, Escheria coli, Pseudomonas aeruginosa* |
| Artificial Voice Prosthesis | *Candida albicans, Streptococcus mitis, Streptococcus salivarius, Rothia dentrocacirosa, Candida tropicalis, Streptococcus sobrhius, Staphylococcus epidermidis, Stomatoccus mucliginous* |
| Intraurterine Device | *Staphyloccus epidermis, Cornybacterium* species, *Staphyloccus aureus, Micrococcus* species, *Lactobacillus plantarum*, groupB *streptocci, Enterococcus* species, *Candida alibcans* |

Unless otherwise defined, all technical and scientific terms used herein have the same meaning as commonly understood by one of ordinary skill in the art to which this invention belongs. Methods and materials are described herein; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Various terms relating to the methods and other aspects of the disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, ±0.5%, ±0.4%, ±0.3%, ±0.2%, ±0.1%, ±0.09%, ±0.08%, ±0.07%, ±0.06%, ±0.05%, ±0.04%, ±0.03%, ±0.02% or ±0.01% from the specified value, as such variations are appropriate to perform the disclosed methods. The percentages may be interpreted as a percentage of the total mass of the composition disclosed herein or the percentage of weight total mass or volume.

The term "active state" refers to the conformation or set of conformations of a polypeptide or amino acid that allows functional domain or domains of the polypeptide or amino acid to associate or disassociate with another compound, macromolecule, or ligand. In some embodiments, the association or disassociation of the polypeptide or amino acid with another compound, macromolecule, or ligand may propagate or inhibit a biologic signal propagated by the bacterial species or fungal species colonized or growing on a surface and/or in a subject.

The term "administering" or "administration" and the like, refers to providing one or a plurality of compositions or amino acids of the disclosure to the subject in need of treatment. Preferably the subject is a mammal, such as a human. The present disclosure also relates to administering one or a plurality of the compositions of amino acids of the disclosure in conjunction with one or more antibiotics, such as a β-lactam antibiotic. When one or a plurality of the compositions or amino acids of the disclosure are administered in conjunction with an antibiotic, the one or a plurality of the compositions of amino acids in the disclosure and the antibiotic can be administered simultaneously in the same composition, simultaneously in different dosage forms or sequentially or at different times. When the one or a plurality of compositions of amino acids of the disclosure and the antibiotic are administered at the same time, they can be administered as a single composition or pharmaceutical composition or they can be administered as separate pharmaceutical compositions. It is understood that when one or a plurality of the compositions of amino acids of the disclosure are administered, one or a plurality of the compositions of amino acids of the disclosure can be administered in conjunction with an antibiotic, that the active agents can be administered in a single combination or in multiple combinations. For example, when administered intravenously, the one or a plurality of the compositions of amino acids in the disclosure can be dissolved or suspended in any of the commonly used intravenous fluids and administered by infusion, and then an antibiotic can be dissolved or suspended in any of the commonly used intravenous fluids and administered by infusion. Conversely, the antibiotic can be dissolved or suspended in any of the commonly used intravenous fluids and administered by infusion, and then one or a plurality of compositions of amino acids of the disclosure can be dissolved or suspended in any of the commonly used intravenous fluids and administered by infusion. Alternatively, a pharmaceutical composition comprising one or a plurality of the compositions of amino acids in the disclosure and an antibiotic can be dissolved or suspended in any of the commonly used intravenous fluids and administered by infusion.

The terms "amino acid" refers to a molecule containing both an amino group and a carboxyl group bound to a carbon which is designated an alpha-carbon. Amino acid also refers to or includes, without limitation, both the D- and L-isomers of the naturally-occurring amino acids, as well as non-naturally occurring amino acids prepared by organic synthesis or other metabolic routes. In some embodiments, a single "amino acid" might have multiple sidechains moieties, as available per an extended aliphatic or aromatic backbone scaffold. In some embodiments, the compositions comprise amino acids with non-natural side chains. Unless the context specifically indicates otherwise, the term amino acid, as used herein, is intended to include amino acid analogs. In some embodiments, the amino acids of the disclosure include only those L-isomers or combinations of L-isomers with other non-natural amino acids. In some embodiments, the compositions, pharmaceutical compositions, or decontamination solutions are free of D-isomers of any naturally occurring non-bonded amino acid or salts thereof. In some embodiments, the composition or pharmaceutical composition of the disclosure comprises a therapeutically effective amount of at least one non-bonded amino acid or a pharmaceutically acceptable salt thereof. In some embodiments, the amino acid may be a non-bonded natural or non-natural amino acid or a pharmaceutically acceptable salt thereof. In the case of non-natural amino acids, the non-bonded amino acid or salt thereof, in some embodiments, is modified with non-natural chemical substituents on its side chain and/or amino terminus and/or carboxy terminus. In some embodiments, the non-bonded amino acid is an isomer or optical isomer of the natural amino acid from which it is derived.

As used herein, the term "derived from" in the context of the relationship between a chemical structure or amino acid sequence and a related chemical structure or related amino acid sequence describes a chemical structure or amino acid sequence that may be homologous to or structurally similar to the related chemical structure or related amino acid sequence. For instance, norleucine is an amino acid derived from leucine because it comprises a chemical formula substantively based upon the chemical formula of leucine.

As used herein "therapeutically effective amount" refers to an amount of a compound, material, or composition, as described herein effective to achieve a particular biological result such as, but not limited to, biological results disclosed, described, or exemplified herein. Such results may include, but are not limited to, the effective reduction of signs and symptoms associated with any bacterial or fungal infection of the disease states mentioned herein, as determined by any means suitable in the art. Such results may include, but are not limited to, the effective disruption of bacterial biofilm growth or maintenance, the effective disruption of fungal biofilm growth or maintenance, or the reduction of clinically relevant numbers of bacterial or fungal cells at or proximate to the surface of an implanted or non-implanted medical device or surface intended to be sterile. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. A therapeutically effective amount of the compositions or pharmaceutical compositions described herein may provide partial or complete cure or resolution of signs and symptoms associated with the bacterial or fungal infections of the subject being treated as compared to the signs and symptoms or infection of a subject infected by the bacterial or fungal species disclosed herein who is left untreated. A therapeutically effective dose of the amino acids described herein may provide a sustained biochemical or biological effect and/or an increased resistance to bacterial or fungal infection or biofilm formation when administered to a subject as compared to the same subject were it left untreated.

The term "non-bonded" amino acid encompasses a single amino acid or pharmaceutically acceptable salt thereof with a free amino or carboxy group not covalently bound to another molecule or chemical substance. In some embodiments, the composition, pharmaceutical composition or decontamination solution of the disclosure comprises a naturally occurring amino acid or a non-naturally occurring amino acid in a solid dosage form or liquid dosage form that is not covalently bound to a molecule or chemical substance. In some embodiments, the compositions, pharmaceutical compositions or decontamination solution of the disclosure comprises a non-bonded amino acid salt which may be complexed with a buffer, salt or other small chemical compound, but the amino acid is not integrated within a polypeptide. In some embodiments, the composition, pharmaceutical composition or decontamination solution of the present disclosure comprises one or more amino acids that are bound to a chemical group or substituent that when administered to a surface or a subject and exposed to a pharmacologically active substance (environmentally available or physiologically available in a subject) is cleaved to form a free amino acid not covalently bound to a component of the composition, pharmaceutical composition or decontamination solution. This form would be considered a pro-drug form of the amino acid. "Non-bonded" forms of the claimed amino acids include those pro-drug forms that may or may not have a cleavable substituent that, under therapeutically effective conditions, cleaved from the amino acid or amino acids in the composition.

A "non-natural side chain" is a modified or synthetic chain of atoms joined by a covalent bond to the α-carbon atom, β-carbon atom, or γ-carbon atom which does not make up the backbone of the polypeptide chain of amino acids. The natural side chain, or R group, of alanine is a methyl group. In some embodiments, the non-natural side chain of the composition is a methyl group in which one or more of the hydrogen atoms is replaced by a deuterium atom.

The term "polypeptide" encompasses two or more naturally or non-naturally-occurring amino acids joined by a covalent bond (e.g., an amide bond). Polypeptides as described herein include full-length proteins (e.g., fully processed pro-proteins or full-length synthetic polypeptides) as well as shorter amino acid sequences (e.g., fragments of naturally-occurring proteins or synthetic polypeptide fragments) that comprise or are free of carbohydrate modifications.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts of the embodiments include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising one or may be formed by reacting the free base, or a salt, enantiomer or racemate thereof, with one or more equivalents of the appropriate acid. In some embodiments, pharmaceutical acceptable salts refer to amino acids having at least one basic group or at least one basic radical. In some embodiments, pharmaceutical acceptable salts comprise a free amino group, a free guanidino group, a pyrazinyl radical, or a pyridyl radical that forms acid addition salts. In some embodiments, the pharmaceutically acceptable salts refer to amino acids that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts described herein can be in their anhydrous form or in hydrated crystalline form (i.e., complexed or crystallized with one or more molecules of water).

The term "soluble" or "water soluble" refers to solubility that is higher than $1/100,000$ (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is $1/10,000$ (mg/ml) or less. Water soluble or soluble substances include, for example, polyethylene glycol. In some embodiments, the modified or natural amino acid of the claimed invention may be bound by polyethylene glycol to better solubilize the composition comprising the peptide of the amino acid.

The term "subject" is used throughout the specification to describe an animal to whom treatment with the compositions is provided or administered. For treatment of those conditions which are specific for a specific subject, such as a human being, the term "patient" may be interchangeably used. In some instances, the term "patient" refers to human patients. In some embodiments, the subject may be a mammal. In some embodiments, the subject may be a non-mammalian animal. In some embodiments, the subject is a domesticated mammal such as a canine, equine, feline, porcine, bovine, murine, caprine, ovine, or other domesticated mammal. In some embodiments, the subject is a human.

The terms "treating" and "to treat", mean to alleviate signs and/or symptoms, eliminate the causation either on a temporary or permanent basis, or to prevent or slow the appearance of symptoms. The term "treatment" includes alleviation, elimination of causation (temporary or permanent) of, or prevention of signs and/or symptoms and disorders associated with any condition, such as a fungal infection, bacterial infection, or either of those types of infections comprising microorganisms in the form of a biofilm. The treatment may be a pre-treatment (as a preventative treatment) and/or treatment at the onset of signs and/or symptoms.

Pharmaceutical Compositions

An object of the disclosure is a pharmaceutical composition comprising one or a plurality of non-bonded amino acids in a therapeutically effective amount. In some embodiments, the non-bonded amino acid or amino acids of the composition may be in a liquid dosage form but dissolved at a concentration of from about 0.1% to about 10% weight per volume. In some embodiments, the non-bonded amino acid or amino acids of the composition may be in a liquid dosage form but dissolved at a concentration of from about 0.1% to about 10% weight per volume, wherein the composition is free of any one or plurality of non-bonded amino acids from Tables D and E at a concentration of about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, 1.0% or more. In some embodiments, the dissolved concentration is about 0.5% weight per volume of solution. In some embodiments, the dosage form is free of any one or plurality of non-bonded amino acids disclosed in Tables D and E. In some embodiments, the dosage form is free of any one or plurality of non-bonded amino acids identified as an amino acid having a neutral effect in forming or disrupting a bacterial and/or fungal biofilm in Tables D and E. In some embodiments, the dosage form is free of any one or plurality of non-bonded amino acids identified as an amino acid encouraging the formation of a biofilm in Tables D and E. In some embodiments, the dosage form is free of any one or plurality of non-bonded amino acids identified in Tables D and E as an amino acid that positively contributes to the inhibition of bacterial and/or fungal biofilm formation or maintenance. For example, pharmaceutical compositions of the disclosure may comprise from about 0.1% to about 5.0% weight to volume of any one non-bonded amino acid in columns 1 or 2 from Tables D and E but also be free of any other non-bonded amino acid in columns 1 or 2 from Tables D and E. In some embodiments, any of the compositions disclosed herein may comprise any one or plurality of amino acids or slats thereof identified as Neutral in Tables D and E.

The disclosure relates to pharmaceutical compositions comprising a first non-bonded amino acid explicitly not comprising or being free of a second, third, fourth or more non-bonded amino acid, where addition of second, third, fourth or more non-bonded amino acid may have a deleterious effect on inhibition of biofilm formation or maintenance. In some embodiments, to be "free of" the non-bonded amino acid in the composition may refer to free of an amount sufficient to cause a deleterious effect on the inhibition of biofilm formation or maintenance, such that addition of that amount encourages formation of or stability of a bacterial or fungal biofilm, or, in the case of "neutral effect" does not have an effect on either destroying or encouraging formation of the bacterial or fungal biofilms. In some embodiments, to be "free of" a particular amino acid means that the composition or pharmaceutical composition disclosed herein is free of a percentage weight to volume of one or a plurality of non-bonded amino acids or salts thereof equal to no greater than about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0%. It is understood that the term "free of" in some embodiments is meant to mean that the non-bonded amino acid is absent in the composition, in trace amounts or at a concentration that would not affect the biological effect of an effective amount of one or more amino acids that have a disruptive or inhibitory effect on the bacterial and/or fungal biofilm formation or maintenance. In some embodiments, to be "free of" a particular amino acid means that the composition or pharmaceutical composition disclosed herein is free of a particular percentage weight to volume of one or a plurality of non-bonded amino acids or salts thereof identified in Tables D and E. For instance if the composition of pharmaceutical composition comprises a first non-bonded amino acid and is "free of" the second or more non-bonded amino acids, the embodiments include the composition or pharmaceutical composition disclosed herein wherein the second or more non-bonded amino acid is not present at an independently discrete concentration or range, such as about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0% for the second a non-bonded amino acid and any other discrete concentration or percentage in respect to any third, fourth, fifth or more amino acid. In some embodiments, the composition or pharmaceutical composition is free of one or a plurality of non-bonded amino acids at a concentration of X nM, wherein X is any positive integer from about 1 to about 10,000. Any range of from about 1 to about any positive integer to about 10,000 is contemplated by the embodiment.

In some embodiments, the pharmaceutical composition or formulation disclosed herein comprise a range of any one or plurality of one or plurality of disclosed non-bonded amino acids from about 0.1% to about 0.39% in weight to volume of solution. In some embodiments, the pharmaceutical composition or formulation disclosed herein comprise a range of any one or plurality of one or plurality of disclosed non-bonded amino acids from about 0.41% to about 5.0% in weight to volume of solution. In some embodiments, the pharmaceutical composition or formulation disclosed herein comprise a range of any one or plurality of one or plurality of disclosed non-bonded amino acids from about 0.1% to about 0.39% in weight to volume of solution and any one or plurality of one or plurality of disclosed non-bonded amino acids from about 0.41% to about 5.0% in weight to volume of solution. In some embodiments, the pharmaceutical composition or formulation disclosed herein comprise a range of any one or plurality of one or plurality of disclosed non-bonded amino acids from about 0.49% to about 0.51% in weight to volume of solution.

An object of the disclosure is a pharmaceutical composition or formulation comprising non-bonded amino acids of the disclosure or salts thereof, and, optionally, further comprising an antibiotic or antifungal agent. In some embodiments, the pharmaceutical compositions or formulations comprise amino acids disclosed herein, or salts thereof, further comprising an antibiotic or antifungal agent.

In some embodiments, the composition comprises non-bonded beta-alanine, or a pharmaceutically acceptable salt thereof, at a weight to volume percent from about 0.1% to about 5.0%; non-bonded 2-aminoadipic acid, or a pharmaceutically acceptable salt thereof, at a weight to volume percent from about 0.1% to about 5.0%; non-bonded aspartic acid, or a pharmaceutically acceptable salt thereof, at a weight to volume percent from about 0.1% to about 5.0%; non-bonded cystathionine (0.2%), or a pharmaceutically acceptable salt thereof, at a weight to volume percent from about 0.1% to about 5.0%; non-bonded cysteine, or a pharmaceutically acceptable salt thereof, at a weight to volume percent from about 0.1% to about 5.0%; non-bonded ethanolamine, or a pharmaceutically acceptable salt thereof, at a weight to volume percent from about 0.1% to about 5.0%; non-bonded glutamic acid, or a pharmaceutically acceptable salt thereof, at a weight to volume percent from about 0.1% to about 5.0%, non-bonded homocysteine, or a pharmaceutically acceptable salt thereof, at a weight to volume percent from about 0.1% to about 5.0%; non-bonded hydroxyproline, or a pharmaceutically acceptable salt thereof, at a weight to volume percent from about 0.1% to about 5.0%; non-bonded phosphoethanolamin, or a pharmaceutically acceptable salt thereof, at a weight to volume percent from about 0.1% to about 5.0%; non-bonded phosphoserine, or a pharmaceutically acceptable salt thereof, at a weight to volume percent from about 0.1% to about 5.0%.

In some embodiments, the pharmaceutical compositions or formulations of the disclosure comprise one or a plurality of compounds of Tables D and E. In some embodiments, the pharmaceutical compositions or formulations of the disclosure are free of one or a plurality of non-bonded alanine, non-bonded arginine, non-bonded asparagine, non-bonded valine, non-bonded citrulline, non-bonded glycine, non-bonded isoleucine, non-bonded leucine, non-bonded lysine, non-bonded methionine, non-bonded 3-methylhistidine, non-bonded phenylalanine, non-bonded ornithine, non-bonded proline, non-bonded serine, non-bonded taurine, non-bonded threonine, non-bonded tryptophan, non-bonded valine.

Any of the above compositions or formulations may further comprise salts of any amino acid and/or may further comprise an antibiotic. In some embodiments, the compositions or formulations may further comprise an antifungal compound or molecule. In some embodiments, the compositions or formulations may further comprise an antibacterial compound or molecule.

The pharmaceutical compositions can be formulated for the therapeutic or prophylactic treatment of diseases, such as bacterial infections or fungal infections or for treatment of bacterial cells and/or fungal cells that are in a biofilm state.

In some embodiments, the pharmaceutical composition is formulated for administration intravenously, topically, irrigation of wounds either as wound dressing or in sterile solution, intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment of oral candidiasis, transmucosal, or transdermal delivery.

The pharmaceutical preparations disclosed herein may be prepared in accordance with standard procedures and are administered at dosages that are selected to reduce, prevent or eliminate biofilm formation or maintenance (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein (e.g. one or more amino acid compositions), optionally further comprising a second composition such as an antibiotic or antifungal agent, in association with one or more nontoxic, pharmaceutically-acceptable carriers and/or diluents and/or adjuvants and/or excipients. As used herein, the phrase "pharmaceutically acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Non-limiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Dosage forms may comprise tablet binders, lubricants and or flavoring agents. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, the compounds described herein (e.g. amino acid compositions) optionally comprise, in conjunction with an antibiotic, can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%. In some embodiments, the compositions are free of cysteine or a salt thereof at 0.4% weight to volume in a liquid solution. In some embodiments, the compositions are free of aspartic acid at 0.4% weight or a salt thereof to volume in a liquid solution. In some embodiments, the compositions are free of glutamic acid or a salt at 0.4% weight to volume in a liquid solution. In some embodiments, the compositions are free of glutamic acid or a salt thereof at 0.4% weight to volume in a liquid solution. In some embodiments, the amino acid or amino acid compositions disclosed herein are free of any one or plurality of amino acids or salts thereof at a concentration of about 0.4 grams per ounce of solution.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition (e.g. amino acid compositions) optionally in conjunction with an antibiotic or an antifungal agent, can be dissolved or suspended in any of the commonly used intravenous fluids and administered by infusion. Intravenous fluids include, without limitation, physiological saline or Ringer's solution. Intravenous administration may be accomplished by using, without limitation, syringe, mini-pump or intravenous line.

Pharmaceutical compositions of this disclosure (e.g. amino acid compositions) for parenteral injection comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use or storage.

Solid dosage forms for oral administration include capsules, tablets, pills, powders, and granules. Such forms may include forms that dissolve or disintegrate quickly in the oral environment. In such solid dosage forms, the active compound preferably a non-bonded cysteine (optionally with or without a non-bonded aspartic acid and/or a non-bonded glutamic acid) can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. No. 4,452,775 (issued to Kent), U.S. Pat. No. 5,039,660 (issued to Leonard), and U.S. Pat. No. 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

Alternatively, delayed absorption of a parenterally administered drug form can be accomplished by dissolving or suspending the drug in an oil vehicle.

For intramuscular preparations, a sterile formulation of compounds, optionally in conjunction with an antibiotic, or suitable soluble salt forms thereof, for example hydrochloride salts, can be dissolved and administered in a pharmaceutical diluent such as Water-for-Injection (WFI), physiological saline or about 5% glucose or about 3% glycerol. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds, preferably a composition, pharmaceutical composition or formulation disclosed herein in conjunction with an antibiotic or an antifungal agent, may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions, preferably a composition, pharmaceutical composition or formulation disclosed herein in conjunction with an antibiotic or anti-fungal agent, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal and vaginal administration, the pharmaceutical compositions, pharmaceutical composition or formulation disclosed herein in conjunction with an antibiotic or anti-fungal agents, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably a composition, pharmaceutical composition or formulation disclosed herein in conjunction with an antibiotic, can be a solution of one or more compounds, or salts thereof, in a suitable diluent, in sterile hermetically sealed ampoules or sterile syringes. The concentration of the compounds, preferably a composition, pharmaceutical composition or formulation disclosed herein in conjunction with an antibiotic, in the unit dosage may vary, e.g. from about 1 percent to about 50 percent, depending on the compound used and its solubility and the dose desired by the physician. If the compositions contain dosage units, each dosage unit can contain from about 1 to about 500 mg of the active material. For adult human treatment, the dosage employed can range from about 5 mg to about 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds, preferably in combination with an antibiotic for the drugs in the art-recognized protocols.

Exemplary procedures for delivering an antibacterial agent are described in U.S. Pat. Nos. 6,468,967; 6,852,689; and 5,041,567, issued to Rogers and in PCT patent application number EP94/02552 (publication no. WO 95/05384), the disclosures of which are incorporated by reference in their entireties. In one embodiment, one or more compounds of the invention, preferably compounds and formulations disclosed herein in conjunction with an antibiotic, or pharmaceutical compositions thereof are administered orally, rectally or via injection e.g. intravenous, intramuscular or subcutaneous. In another embodiment, one or more compounds of the invention, preferably a composition, pharmaceutical composition or formulation disclosed herein in conjunction with an antibiotic or anti-fungal, or pharmaceutical compositions thereof are administered orally, rectally or via injection e.g. intravenous, intramuscular or subcutaneous to treat an infection caused by β-lactamase producing bacteria.

For preparing pharmaceutical compositions from the compounds of this invention, pharmaceutical compositions may comprise inert, pharmaceutically acceptable carriers in either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like. Salts include, but are not limited to, pharmaceutically acceptable salts. Examples of pharmaceutically acceptable salts include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and benzathine.

In some embodiments, pharmaceutical compositions comprise pharmaceutically acceptable salts such as hydrochlorides, sulfates and bitartrates. The hydrochloride and sulfate salts are particularly preferred.

The term composition(s) is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins; methyl cellulose, sodium carboxymethyl cellulose, and other suspending agents known to the pharmaceutical formulation art.

Preferably the pharmaceutical compositions are in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The pharmaceutical compositions of the instant disclosure or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well-established principles and compositions described in, for example, Remington: The Science and Practice of Pharmacy, 19th Edition, 1995; British Pharmacopoeia 2000, each of which is incorporated herein by reference. The compositions of may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but are not limited to, acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricants include, but are not limited to, such slippery solids as talc, magnesium and calcium stearate, stearic acid and hydrogenated vegetable oils.

Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also contemplated are liquid formulations and solid form preparations which are intended to be converted, shortly before use, to liquid form preparations. Such liquid forms include, but are not limited to, solutions, suspensions, syrups, slurries, and emulsions.

Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In some embodiments, the oral transmucosal solid dosage further comprises a permeation enhancer. In some embodiments, the permeation enhancer is chosen from: a bile salt, sodium dodecyl sulfate, dimethyl sulfoxide, sodium lauryl sulfate, a derivative of a saturated or a unsaturated fatty acid, a surfactant, a bile salt analog, and a derivative of a bile salt. In some embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In some embodiments, the oral transmucosal solid dosage form of wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. The invention is directed to an oral transmucosal solid dosage form comprising from wherein the concentration of analog is from about 0.01% to about 90% of the dry matter weight of the composition.

Solid dosage forms such as lozenges and tablets may also be used for oral delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug. Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation. A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain signs and/or symptoms, such as pain, nausea, motion sickness, and premedication prior to anesthesia because each patient needs a different amount of medication to treat these signs and/or symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery. Of course, as the solid dosage form dissolves in the oral cavity, some of the saliva containing the pharmaceutical agent may be swallowed, and a portion of the drug may ultimately be absorbed from the intestines.

The compositions of the invention can be administered in a sustained release composition, such as those described in, for example, U.S. Pat. Nos. 5,672,659 and 5,595,760, and herein incorporated by reference in their entireties. The use of immediate or sustained release compositions depends on the type of condition being treated.

The pharmaceutical compositions or the pharmaceutical acceptable salts derived therefrom may be in a dosage amount in an effective amount to induce death or disruption of biofilms of bacterial or fungal cells. The pharmaceutical compositions or the pharmaceutical acceptable salts derived therefrom may be in an effective amount to reduce the growth rate or inhibiting the formation of a biofilm of a bacterial or fungal species. The pharmaceutical compositions or the pharmaceutical acceptable salts derived therefrom may be in a dosage amount for an effective amount to reduce or eliminate the signs and/or symptoms of a bacterial or fungal infection in a subject.

The dose of the composition or pharmaceutical compositions may vary. The dose of the composition may be once per day. In some embodiments, multiple doses may be administered to the subject daily. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses. In some embodiments, the methods of administering the pharmaceutical compositions of the disclosure comprise application or administration periods of once an hour, once every two hours, once every 6 hours, once every 12 hours or once a day. In some embodiments, the methods of administering the pharmaceutical compositions of the disclosure comprise application or administration periods of twice an hour or more frequently depending upon the severity of the infection of contamination or to prevent toxic side-effects from destruction of the pathogen.

In some embodiments, subjects can be administered the composition in which the composition is provided in a daily dose range of about 0.0001 mg/kg to about 5000 mg/kg of the weight of the subject. The dose administered to the subject can also be measured in terms of total amount of amino acid administered per day. In some embodiments, a subject is administered from about 0.001 to about 3000 milligrams of amino acid per day. In some embodiments, a subject is administered up to about 2000 milligrams of amino acid per day. In some embodiments, a subject is administered up to about 1800 milligrams of amino acid per day. In some embodiments, a subject is administered up to about 1600 milligrams of amino acid per day. In some embodiments, a subject is administered up to about 1400 milligrams of amino acid per day. In some embodiments, a subject is administered up to about 1200 milligrams of amino acid per day. In some embodiments, a subject is administered up to about 1000 milligrams of amino acid per day. In some embodiments, a subject is administered up to about 800 milligrams of amino acid per day. In some embodiments, a subject is administered from about 0.001 milligrams to about 700 milligrams of amino acid per dose. In some embodiments, a subject is administered up to about 700 milligrams of amino acid per dose. In some embodiments, a subject is administered up to about 600 milligrams of amino acid per dose. In some embodiments, a subject is administered up to about 500 milligrams of amino acid per dose. In some embodiments, a subject is administered up to about 400 milligrams of amino acid per dose. In some embodiments, a subject is administered up to about 300 milligrams of amino acid amino acid per dose. In some embodiments, a subject is administered up to about 200 milligrams of amino acid per dose. In some embodiments, a subject is administered up to about 100 milligrams of amino acid per dose. In some embodiments, a subject is administered up to about 50 milligrams of amino acid per dose.

In some embodiments, subjects can be administered the composition in which the composition comprising an amino acid or pharmaceutically acceptable salt thereof is administered in a daily dose range of about 0.0001 mg/kg to about 5000 mg/kg of the weight of the subject. In some embodiments, the composition comprising an amino acid or amino acid composition or pharmaceutically acceptable salt thereof is administered in a daily dosage of up about 450 mg/kg of the weight of the subject. In some embodiments, the composition comprising an amino acid or amino acid composition or pharmaceutically acceptable salt thereof is administered in a daily dosage of up about 400 mg/kg of the weight of the subject. In some embodiments, the composition comprising an amino acid or amino acid composition or pharmaceutically acceptable salt thereof is administered in a daily dosage of up about 350 mg/kg of the weight of the subject. In some embodiments, the composition comprising an amino acid or amino acid composition or pharmaceutically acceptable salt thereof is administered in a daily dosage of up about 300 mg/kg of the weight of the subject. In some embodiments, the composition comprising an amino acid or amino acid composition or pharmaceutically acceptable salt thereof is administered in a daily dosage of up about 250 mg/kg of the weight of the subject. In some embodiments, the composition comprising an amino acid or amino acid composition or pharmaceutically acceptable salt thereof is administered in a daily dosage of up about 200 mg/kg of the weight of the subject. In some embodiments, the composition comprising an amino acid or amino acid composition or pharmaceutically acceptable salt thereof is administered in a daily dosage of up about 150 mg/kg of the weight of the subject. In some embodiments, the composition comprising an amino acid or amino acid composition or pharmaceutically acceptable salt thereof is administered in a daily dosage of up about 100 mg/kg of the weight of the subject. In some embodiments, the composition comprising an amino acid or amino acid composition or pharmaceutically acceptable salt thereof is administered in a daily dosage of up about 50 mg/kg of the weight of the subject. In some embodiments, the composition comprising an amino acid or amino acid composition or pharmaceutically acceptable salt thereof is administered in a daily dosage of up about 25 mg/kg of the weight of the subject.

In some embodiments, the composition comprising an amino acid or amino acid composition or pharmaceutically acceptable salt thereof is administered in a daily dosage of up about 10 mg/kg of the weight of the subject. In some embodiments, the composition comprising an amino acid or amino acid composition or pharmaceutically acceptable salt thereof is administered in a daily dosage of up about 5 mg/kg of the weight of the subject. In some embodiments, the composition comprising an amino acid or amino acid composition or pharmaceutically acceptable salt thereof is administered in a daily dosage of up about 1 mg/kg of the weight of the subject. In some embodiments, the composition comprising an amino acid or amino acid composition or pharmaceutically acceptable salt thereof is administered in a daily dosage of up about 0.1 mg/kg of the weight of the subject. In some embodiments, the composition comprising an amino acid or amino acid composition or pharmaceutically acceptable salt thereof is administered in a daily dosage of up about 0.01 mg/kg of the weight of the subject. In some embodiments, the composition comprising an amino acid or amino acid composition or pharmaceutically acceptable salt thereof is administered in a daily dosage of up about 0.001 mg/kg of the weight of the subject. The dose administered to the subject can also be measured in terms of total amount of amino acid or amino acid composition administered per day.

In some embodiments, a subject in need thereof is administered from about 1 ng to about 500 µg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µg to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 10 mg. of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µg to about 900 µg of analog or pharmaceutically salt thereof per day. In some embodiments, a subject in need thereof is administered from about 900 µg to about 1 mg of analog or pharmaceutically salt thereof per day.

In some embodiments, a subject in need thereof is administered from about 0.0001 to about 3000 milligrams of amino acid or amino acid composition or pharmaceutically salt thereof per day. In some embodiments, a subject is administered up to about 2000 milligrams of amino acid or amino acid composition or pharmaceutically salt thereof day. In some embodiments, a subject is administered up to about 1800 milligrams of amino acid or amino acid composition or pharmaceutically salt thereof per day. In some embodiments, a subject is administered up to about 1600 milligrams of amino acid or amino acid composition or pharmaceutically salt thereof per day. In some embodiments, a subject is administered up to about 1400 milligrams of amino acid or amino acid composition or pharmaceutically salt thereof per day. In some embodiments, a subject is administered up to about 1200 milligrams of amino acid or amino acid composition or pharmaceutically salt thereof per day. In some embodiments, a subject is administered up to about 1000 milligrams of amino acid or amino acid composition or pharmaceutically salt thereof per day. In some embodiments, a subject is administered up to about 800 milligrams of amino acid or amino acid composition or pharmaceutically salt thereof per day. In some embodiments, a subject is administered from about 0.0001 milligrams to about 700 milligrams of amino acid or amino acid composition or pharmaceutically salt thereof per dose. In some embodiments, a subject is administered up to about 700 milligrams of amino acid or amino acid composition or pharmaceutically salt thereof per dose. In some embodiments, a subject is administered up to about 600 milligrams of amino acid or amino acid composition or pharmaceutically salt thereof per dose. In some embodiments, a subject is administered up to about 500 milligrams of amino acid or amino acid composition or pharmaceutically salt thereof per dose. In some embodiments, a subject is administered up to about 400 milligrams of amino acid or amino acid composition or pharmaceutically salt thereof per dose. In some embodiments, a subject is administered up to about 300 milligrams of amino acid or amino acid composition or pharmaceutically salt thereof per dose. In some embodiments, a subject is administered up to about 200 milligrams of amino acid or amino acid composition or pharmaceutically salt thereof per dose. In some embodiments, a subject is administered up to about 100 milligrams of amino acid or amino acid composition or pharmaceutically salt thereof per dose. In some embodiments, a subject is administered up to about 50 milligrams of amino acid or amino acid composition or pharmaceutically salt thereof per dose. In some embodiments, a subject is administered up to about 25 milligrams of amino acid or amino acid composition or pharmaceutically salt thereof per dose. In some embodiments, a subject is administered up to about 15 milligrams of amino acid or amino acid composition or pharmaceutically salt thereof per dose.

In some embodiments, a subject is administered up to about 10 milligrams of amino acid or amino acid composition or pharmaceutically salt thereof per dose. In some embodiments, a subject is administered up to about 5 milligrams of amino acid or amino acid composition or pharmaceutically salt thereof per dose. In some embodiments, a subject is administered up to about 1 milligram of Amino acid or amino acid composition or pharmaceutically salt thereof per dose. In some embodiments, a subject is administered up to about 0.1 milligrams of amino acid or amino acid composition or pharmaceutically salt thereof per dose. In some embodiments, a subject is administered up to about 0.001 milligrams of amino acid or amino acid composition or pharmaceutically salt thereof per dose.

The dose administered to the subject can also be measured in terms of total amount of amino acid or amino acid composition or pharmaceutical salt thereof administered per ounce of liquid prepared. In some embodiments, the amino acid or amino acid composition or pharmaceutical salt thereof is at a concentration of from about 0.000001 grams per ounce of solution to about 2.5 grams per ounce of solution. In some embodiments, the amino acid or amino acid composition or pharmaceutical salt thereof is at a concentration of about 2.25 grams per ounce of solution. In some embodiments, the Amino acid or amino acid composition or pharmaceutically salt thereof is at a concentration of about 2.25 grams per ounce of solution. In some embodiments, the amino acid or amino acid composition or pharmaceutically salt thereof is at a concentration of about 2.0 grams per ounce of solution. In some embodiments, the amino acid or amino acid composition or pharmaceutically salt thereof is at a concentration of about 1.9 grams per ounce of solution. In some embodiments, the amino acid or amino acid composition or pharmaceutically salt thereof is at a concentration of about 1.8 grams per ounce of solution. In some embodiments, the amino acid or amino acid composition or pharmaceutically salt thereof is at a concentration of about 1.7 grams per ounce of solution. In some embodiments, the amino acid or amino acid composition or pharmaceutically salt thereof is at a concentration of about 1.6 grams per ounce of solution. In some embodiments, the amino acid or amino acid composition or pharmaceutically salt thereof is at a concentration of about 1.5 grams per ounce of solution. In some embodiments, the amino acid or amino acid composition or pharmaceutically salt thereof is at a concentration of about 1.4 grams per ounce of solution. In some embodiments, the amino acid or amino acid composition or pharmaceutically salt thereof is at a concentration of about 1.3 grams per ounce of solution. In some embodiments, the amino acid or amino acid composition or pharmaceutically salt thereof is at a concentration of about 1.2 grams per ounce of solution. In some embodiments, the amino acid or amino acid composition or pharmaceutically salt thereof is at a concentration of about 1.1 grams per ounce of solution. In some embodiments, the amino acid or amino acid composition or pharmaceutically salt thereof is at a concentration of about 1.0 grams per ounce of solution.

In some embodiments, the amino acid or amino acid composition or pharmaceutically salt thereof is at a concentration of about 0.9 grams per ounce of solution. In some embodiments, the amino acid or amino acid composition or pharmaceutically salt thereof is at a concentration of about 0.8 grams per ounce of solution. In some embodiments, the amino acid or amino acid composition or pharmaceutically salt thereof is at a concentration of about 0.7 grams per ounce of solution. In some embodiments, the amino acid or amino acid composition or pharmaceutically salt thereof is at a concentration of about 0.6 grams per ounce of solution. In some embodiments, the amino acid or amino acid composition or pharmaceutically salt thereof is at a concentration of about 0.5 grams per ounce of solution. In some embodiments, the amino acid or amino acid composition or pharmaceutically salt thereof is at a concentration of about 0.4 grams per ounce of solution. In some embodiments, the amino acid or amino acid composition or pharmaceutically salt thereof is at a concentration of about 0.3 grams per ounce of solution. In some embodiments, the amino acid or amino acid composition or pharmaceutically salt thereof is at a concentration of about 0.2 grams per ounce of solution. In some embodiments, the amino acid or amino acid composition or pharmaceutically salt thereof is at a concentration of about 0.1 grams per ounce of solution. In some embodiments, the amino acid or amino acid composition or pharmaceutically salt thereof is at a concentration of about 0.01 grams per ounce of solution. In some embodiments, the amino acid or amino acid composition or pharmaceutically salt thereof is at a concentration of about 0.001 grams per ounce of solution prepared. In some embodiments, the amino acid or amino acid composition or pharmaceutically salt thereof is at a concentration of about 0.0001 grams per ounce of solution prepared. In some embodiments, the amino acid or amino acid composition or pharmaceutically salt thereof is at a concentration of about 0.00001 grams per ounce of solution prepared. In some embodiments, the amino acid or amino acid composition or pharmaceutically salt thereof is at a concentration of about 0.000001 grams per ounce of solution prepared.

Dosage may be measured in terms of mass amount of amino acid per liter of liquid formulation prepared. One skilled in the art can increase or decrease the concentration of the analog in the dose depending upon the strength of biological activity desired to treat or prevent any above-mentioned disorder associated with the treatment of subjects in need thereof. For instance, one embodiment of the invention can include up to 0.00001 grams of amino acid per 100 mL of liquid formulation and up to about 10 grams of amino acid per 100 mL of liquid formulation.

In some embodiments, the amino acids of any of the compositions or pharmaceutical compositions disclosed here may have a dosage measured by percent of 100 mL of volume of liquid. In some embodiments, any of the disclosed amino acids in a composition has a concentration of from about 0.41% to about 0.59% per 100 mL of total volume or per liter of total volume. In some embodiments, any of the disclosed amino acids in a composition has a concentration of from about 0.42% to about 0.5% per 100 mL of total volume or per liter of total volume. In some embodiments, any of the disclosed amino acids in a composition has a concentration of from about 0.43% to about 0.5% per 100 mL of total volume or per liter of total volume. In some embodiments, any of the disclosed amino acids in a composition has a concentration of from about 0.44% to about 0.5% per 100 mL of total volume or per liter of total volume. In some embodiments, any of the disclosed amino acids in a composition has a concentration of from about 0.45% to about 0.5% per 100 mL of total volume or per liter of total volume. In some embodiments, any of the disclosed amino acids in a composition has a concentration of from about 0.46% to about 0.5% per 100 mL of total volume or per liter of total volume. In some embodiments, any of the disclosed amino acids in a composition has a concentration of from about 0.47% to about 0.5% per 100 mL of total volume or per liter of total volume. In some embodiments, any of the disclosed amino acids in a composition has a concentration of from about 0.48% to about 0.5% per 100 mL of total volume or per liter of total volume. In some embodiments, any of the disclosed amino acids in a composition has a concentration of from about 0.49% to about 0.5% per 100 mL of total volume or per liter of total volume. In some embodiments, any of the disclosed amino acids in a composition has a concentration of from about 0.50% to about 6.0% per 100 mL of total volume or per liter of total volume. In some embodiments, any of the disclosed amino acids in a composition has a concentration of from about 0.50% to about 1.0% per 100 mL of total volume or per liter of total volume. In some embodiments, any of the disclosed amino acids in a composition has a concentration of from about 0.50% to about 0.51% per 100 mL of total volume or per liter of total volume.

In some embodiments, any of the disclosed amino acids in a composition has a concentration of from about 0.50% to about 0.52% per 100 mL of total volume or per liter of total volume. In some embodiments, any of the disclosed amino acids in a composition has a concentration of from about 0.50% to about 0.53% per 100 mL of total volume or per liter of total volume. In some embodiments, any of the disclosed amino acids in a composition has a concentration of from about 0.50% to about 0.54% per 100 mL of total volume or per liter of total volume.

In some embodiments, any of the disclosed amino acids in a composition has a concentration of from about 0.50% to about 0.55% per 100 mL of total volume or per liter of total volume. In some embodiments, any of the disclosed amino acids in a composition has a concentration of from about 0.50% to about 0.56% per 100 mL of total volume or per liter of total volume. In some embodiments, any of the disclosed amino acids in a composition has a concentration of from about 0.50% to about 0.57% per 100 mL of total volume or per liter of total volume. In some embodiments, any of the disclosed amino acids in a composition has a concentration of from about 0.50% to about 0.58% per 100 mL of total volume or per liter of total volume. In some embodiments, any of the disclosed amino acids in a composition has a concentration of from about 0.50% to about 0.59% per 100 mL of total volume or per liter of total volume.

In some embodiments the pharmaceutical compositions of the claimed invention comprise at least one other active agent besides the non-bonded amino acid or amino acids disclosed herein. In some embodiments, the one other active agent is an antibiotic or an antifungal agent. In some embodiments, the composition, pharmaceutical composition or decontamination solution comprises one or a plurality of antibiotics or pharmaceutically acceptable salts thereof, each antibiotic at a therapeutically effective amount.

Macrolide antibiotic that can be added to the inventive formulation include, but are not limited to, inter *alia*: tacrolimus, cyclosporine, sirolimus, everolimus, ascomycin, erythromycin, azithromycin, clarithromycin, clindamycin, lincomycin, dirithromycin, josamycin, spiramycin, diacetylmidecamycin, tylosin, roxithromycin, ABT-773, telithromycin, leucomycins, and lincosamide. Other antibiotics include, but are not limited to, aminoglycosides (e.g., streptomycin, amikacin, gentamicin, tobramycin), cephalosporins (e.g., beta lactams including penicillin), tetracyclines, acyclorvir, amantadine, polymyxin B, amphotericin B, amoxicillin, ampicillin, atovaquone, azithromycin, azithromycin, bacitracin, cefazolin, cefepime, cefotaxime, cefotetan, cefpodoxime, ceftazidime, ceftizoxime, ceftriaxone, cefuroxime, cephalexin, chloramphenicol, clotimazole, ciprofloxacin, clarithromycin, clindamycin, dapsone, dicloxacillin, fluconazole, foscarnet, ganciclovir, gatifloxacin, griseofulvin, isoniazid, itraconazole, ketoconazole, metronidazole, nafcillin, neomycin, nitrofurantoin, nystatin, pentamidine, rifampin, rifamycin, valacyclovir, vancomycin, etc. The indications, effective doses, formulations, contraindications, vendors, etc. of these antibiotics are known to one skilled in the art.

In some embodiments of the invention, the antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment of the invention, the antibiotic is a carbapenen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In one embodiment of the invention, the antibiotic is a monobactam. Examples of monobactam antibiotics include, but are not limited to Aztreonam, Tigemonam, Carumonam, BAL30072 and Nocardicin A.

In one embodiment of the invention, the antibiotic is a penem. In one embodiment of the invention, the antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

In one embodiment the cephalosporin is Ceftolozane, Ceftazidime, Aztreonam or Meropenem, or more preferably, Ceftolozane or Ceftazidime.

Antifungal Agents

In some embodiments, the active agent or pharmaceutically acceptable salt thereof is administered with an antifungal agent. For example, in some embodiments, the antifungal agent is a polyene (for instance, amphotericin B), an azole (for instance, fluconazole), an echinocandin (for instance, caspofungin), a nucleoside analog (for instance, 5-fluorocytosine), an allylamine (for instance, naftifine, terbinafine, or butenafine), or other antifungal agents (for instance, ciclopirox). Examples of polyenes include, e.g., nystatin, amphotericin B, and leukotriene, or pharmaceutically acceptable salts thereof. Examples of azoles include miconazole, clotrimazole, ketoconazole, oxiconazole, eberconazole, econazole, sulconazole, sertaconazole, bifonazole, butoconazole, fenticonazole, isoconazole, omoconazole and tioconazole, or pharmaceutically acceptable salts thereof. Examples of echinocandins include caspofungin, pneumocandins, echinocandin B, ciliofungin, micafungin, and anidulafungin, or pharmaceutically acceptable salts thereof. Examples of nucleoside analogs include 5-fluorocytosine, or pharmaceutically acceptable salts thereof. Examples of allylamines include naftifine, terbinafine, and amorolfin, and butenafine, or pharmaceutically acceptable salts thereof. Exemplary other antifungals include ciclopirox, or selenium sulfide. Additional antifungals include agents that block NA synthesis including, e.g., flucytosine, and those that disrupt microtubule function including, e.g., griseofulvin. Suitable antifungals can include one of candicidin, filipin, hamycin, natamycin, and rimocidin. Triazoles, including albaconazole, fluconazole, isavuconazole, itraconazole, posaconazole, ravuconazole, terconazole, and voriconazole are also suitable antifungal active agents. Also suitable are, thiazoles including, e.g., abafungin. Suitable antifungal agents include, e.g., of amorolfin, butenafine, naftifine, and terbinafine. In addition, echinocandins, including anidulafungin, caspofungin, and micafungin, are suitable antifungals. Also suitable are griseofulvin, benzoic acid, ciclopirox, haloprogin, polygodial, tolnaftate, undecylenic acid, and Crystal violet.

Suitable antifungal agents for use in the present topical pharmaceutical compositions include, but are not limited to, natifine, butenafine, terbinafine, and amorolfine, as well as any pharmaceutically acceptable salts thereof. Suitable salts of antifungal agents include but are not limited to hydrochloride salts. In some embodiments, certain antifungal agents or pharmaceutically acceptable salts thereof are believed to act by interfering with squalene 2,3-epoxidase, which results in decreased amounts of the principal membrane sterols, especially ergosterol.

Naftifine and pharmaceutically acceptable salts thereof have fungicidal activity against organisms, including but not limited to, dermatophytes, including for example, *Trichophyton rubrum, Trichophyton interdigitale, Trichophyton verrucosum, Trichophyton mentagrophytes, Trichophyton megninii, Trichophyton tonsurans, Trichophyton schoenleinii, Trichophyton soudanense, Trichophyton violaceum,* Epidermophytonfloccosum, *Microsporum audouini, Microsporum canis, Microsporum distortum, Microsporum gypseum*; nondermatophyte molds including, for example, *Scopulariopsis brevicaulis, Fusarium* spp., *Aspergillus* spp., *Alternaria, Acremonium, Scytalidinum dimidiatum,* and *Scytalidinium hyalinum*; and *Candida* spp. including, for example, *Candida albicans,* and *Candida parapsilosis.*

Butenafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Epidermophyton floccosum, Microsporum canis*; nondermatophyte molds including, for example, *Aspergillus* spp.; *Candida* spp. including, for example, *Candida albicans* and *Candida parapsilosis; Malassezia furfur*; and *Cryptococcus.*

Terbinafine and pharmaceutically acceptable salts thereof, for example, terbinafine hydrochloride, is active against many fungi, including dermatophytes (*Trichophyton, Microsporum, Epidermophyton*), filamentous (e.g. *Aspergillus*), dimorphic (e.g., *Blastomyces*), and dematiaceous fungi and yeasts. Terbinifine has an antifungal spectrum of activity similar to that of naftifine. More specifically, Terbinafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Trichophyton violaceum, Epidermophyton floccosum, Microsporum audouini, Microsporum canis*; nondermatophyte molds including, for example, *Aspergillus* spp. and *Scopulariopsis brevicaulis; Candida* spp. including, for example, *Candida albicans* and *Candida parapsilosis; Blastomyces*; and *Histoplasma.*

Amorolfine and pharmaceutically acceptable salts thereof, for example, amorolfine hydrochloride, is active against many fungi, including dermatophytes (*Trichophyton, Microsporum, Epidermophyton*), filamentous (e.g. *Aspergillus*), dimorphic (e.g., *Blastomyces* and *Sporothrix schenckii*), dematiaceous fungi and yeasts, and *Sporothrix schenckii*. Amorolfine and pharmaceutically acceptable salts thereof, for example, amorolfin hydrochloride, have fungicidal activity against organisms, including but not limited to, dermatophytes including, for example, *Trichophyton rubrum, Trichophyton mentagrophytes, Epidermophyton floccosum*; nondermatophyte molds including, for example, *Scopulariopsis* spp. including *Scopulariopsis brevicaulis, Fusarium* spp. including *Fusarium solani, Aspergillus* spp. including *Aspergillus flavus*, and *Acremonium* spp.; *Candida* spp. including, for example, *Candida albicans* and *Candida parapsilosis*; and *Malassezia* spp. including *Malassezia furfur.*

In some embodiments, an antifungal agent is selected from the group consisting of naftifine, butenafine, terbinafine, and amorolfine. In some embodiments, the antifungal agent is butenafine. In some embodiments, the antifungal agent is terbinafine. In some embodiments, the antifungal agent is amorolfine.

Methods for making the presently described antifungal agents and pharmaceutically acceptable salts thereof are disclosed in U.S. Pat. Nos. 4,755,534; 4,680,291; and 4,282,251, each of which is incorporated by reference herein in its entirety.

The pharmaceutical compositions, preferably a composition of amino acid or amino acids of the disclosure in conjunction with an antibiotic or antifungal agent, can be used to treat a bacterial infection and/or a fungal infection of any organ or tissue or wound in the body of a subject caused by antibiotic-resistant bacteria and/or fungal cells, including, antibiotic-resistant Gram-negative beta-lactam resistant bacteria. These organs or tissue include, without limitation, skeletal muscle, skin, mucous membrane, bloodstream, kidneys, heart, lung, bone, and nervous system. For example, a pharmaceutical composition comprising at least one composition of a non-bonded amino acid or amino acids of the disclosure in conjunction with an antibiotic, can be administered to a subject to treat, without limitation, skin and soft tissue infections (e.g., complex skin infections), bacteremia, intra-abdominal infections and urinary tract infections (e.g., cUTI). In addition, a composition of amino acid or amino acids of the disclosure may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. At least one composition of amino acid or amino acids of the disclosure in conjunction with an antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. At least one composition of amino acid or amino acids of the disclosure optionally in conjunction with an antibiotic, may also be administered to a subject to treat an infection including, without limitation, endocarditis, nephritis, septic arthritis, intra-abdominal sepsis, bone and joint infections, sinusitis, osteomyelitis, and nervous system infection. At least one composition of amino acid or amino acids of the disclosure optionally in conjunction with an antibiotic, or pharmaceutical compositions thereof or pharmaceutically acceptable salt thereof, may also be directly injected or administered into an abscess, ventricle or joint. Pharmaceutical compositions of the disclosure in conjunction with an antibiotic, may be administered as an aerosol for the treatment of pneumonia or other lung-based infections. In one embodiment, the aerosol delivery vehicle is an anhydrous, liquid or dry powder inhaler.

The pharmaceutical compositions disclosed herein may also be used to decontaminate a surface, such as the surface of a biomedical device or an implant.

The pharmaceutical compositions disclosed herein may also further comprise or be administered with one or more active ingredients are chosen from anti-inflammatory agents, antimicrobial active agents, viral bacteriophages, antihistamines, anti-infectives, and nasal decongestants.

In some embodiments, the anti-inflammatory agents are chosen from steroids and non-steroidal anti-inflammatories (NSAIDS).

In some embodiments, the steroids are chosen from prednisone, dexamethasone, and hydrocortisone.

In some embodiments, the steroids are corticosteroids chosen from prednisolone, prednisone, medrol, beclomethsone, budesonide, flunisolide, fluticasone and triamcinolone.

In some embodiments, the anti-inflammatory agents are corticosteroids chosen from dexamethasone, mometasone, and triamcinolone.

In some embodiments, the steroids are corticosteroids chosen from dexamethasone, mometasone, and triamcinolone.

In some embodiments, the NSAIDS are chosen from celecoxib, diclofenac, diflunisal, etodolac, fenoprofen, flurbirofen, ibuprofen, indomethacin, ketoprofen, ketorolac, mefenamic acid, meloxicam, nabumetone, naproxen, oxaprozin, piroxicam, sulindac, tolmetin, acetaminophen, or a newly designed NSAIDS.

In some embodiments, the antimicrobial active agents are chosen from antibiotics, antifungals, and anti-virals.

In some embodiments, the antibiotics are chosen from penicillins, cephalosporins, quinolones, aminoglycosides, amphotericin B, etc.)

In some embodiments, the antibiotics such as penicillins, cephalosporins, macrolides, sulfonamides, quinolones, aminoglycosides, betalactam antibiotics, linezolid, vancomycin; aminoglycosides (including amikacin, gentamicin, kanamycin, neomycin, netilmicin, streptomycin, tobramycin, cephalosporins (including cefadroxil, cefazolin, cefalotin, cefalexin, cefaclor, cefoxitin, cefuroxime, cefixime, cefdinir, cefoperazone, cefotaxime, cefpodoxime, ceftazidime, ceftibuten, ceftriaxone, cefepime, loracarbef, ceftaroline cefobiprole) macrolides (including azithromycin, clarithromycin, erythromycin); penicillins (including amoxicillin, ampicillin, carbenicillin, cloxacillin, dicloxacillin, methicillin, mezlocillin, oxacillin, penicillin, piperacillin, ticarcillin); polypeptides (including bacitracin, colistin, polymyxin b), quinolones ciprofloxacin, levofloxacin, moxifloxacin, norfloxacin, ofloxacin, gatifloxacin, delafloxacin). sulfonamides (including sulfacetamide, sulfadiazine, sulfasalazine, sulfisoxazole, trimethoprim, trimethoprim-sulfamethoxazole); tetracyclines (including demeclocycline, doxycycline, minocycline, oxytetracycline, tetracycline, tigecycline) and others (including chloramphenicol, clindamycin, lincomycin, ethambutol, isoniazid, linezolid, metronidazole, mupirocin, nitrofurantoin, rifampicin, dapsone, imipenem/cilastatin), vancomycin, aztreonam), and all the above antibiotics in combination with efficacy enhancers such as avibactam, tazobactam and clavulanate.

In some embodiments, the antibiotic is chosen from penicillins, cephalosporins, monobactams, carbapenems, macrolides, lincosamides, streptogramins, aminoglycosides, quinolones (fluoroquinolones), sulfonamides, and tetracyclines.

In some embodiments, the penicillins are chosen from amoxicillin, ampicillin, bacampicillin, carbenicillin, cloxacillin, dicloxacillin-flucloxacillin, mezlocillin, nafcillin, oxacillin, penicillin G, penicillin V, piperacillin, pivampicillin, pivmecillinam, ticarcillin, and ticar.

In some embodiments, the cephalosporins are chosen from cefacetrile (cephacetrile), cefadroxil (cefadroxyl), cefalexin (cephalexin), cefaloglycin (cephaloglycin), cefalonium (cephalonium), cefaloridine (cephaloradine), cefalotin (cephalothin), cefapirin (cephapirin), cefatrizine, cefazaflur, cefazedone, cefazolin (cephazolin), cefradine (cephradine), cefroxadine, and ceftezole.

In some embodiments, the cephalosporins are chosen from cefaclor, cefamandole, cefmetazole, cefonicid, cefotetan, cefoxitin, cefprozil (cefproxil), cefuroxime, and cefuzonam.

In some embodiments, the cephalosporins are chosen from cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, and ceftazidime.

In some embodiments, the cephalosporins are chosen from cefclidine, cefepime, cefluprenam, cefoselis, cefozopran, cefpirome, and cefquinome.

In some embodiments, the cephalosporins are chosen from ceftobiprole and ceftaroline.

In some embodiments, the cephalosporins are chosen from cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, and ceftioxide.

In some embodiments, the monobactam is aztreonam.

In some embodiments, the carbapenems are chosen from imipenem, imipenem/cilastatin, doripenem, meropenem, and ertapenem.

In some embodiments, the marcolides are chosen from azithromycin, erythromycin, clarithromycin, dirithromycin, roxithromycin, surlid, and telithromycin.

In some embodiments, the lincosamides are chosen from clindamycin and lincomycin.

In some embodiments, the streptogramins are chosen from pristinamycin and quinupristin/dalfopristin.

In some embodiments, the aminoglycosides are chosen from amikacin, gentamicin, kanamycin, neomycin, netilmicin, paromomycin, streptomycin, and tobramycin.

In some embodiments, the quinolones are chosen from flumequine, nalidixic acid, oxolinic acid, piromidic acid, pipemidic acid, and rosoxacin.

In some embodiments, the quinolones are chosen from ciprofloxacin, enoxacin, lomefloxacin, nadifloxacin, norfloxacin, ofloxacin, pefloxacin, and rufloxacin.

In some embodiments, the quinolones are chosen from balofloxacin, gatifloxacin, grepafloxacin, levofloxacin, moxifloxacin, pazufloxacin, sparfloxacin, temafloxacin, and tosufloxacin.

In some embodiments, the quinolones are chosen from besifloxacin, clinafloxacin, gemifloxacin, sitafloxacin, trovafloxacin, and prulifloxacin.

In some embodiments, the sulfonamides are chosen from sulfamethizole, sulfamethoxazole, sulfisoxazole, and trimethoprim-sulfamethoxazole.

In some embodiments, the tetracyclines are chosen from demeclocycline, doxycycline, minocycline, oxytetracycline, tetracycline, and tigecycline.

In some embodiments, the composition further comprises and efficacy enhancer and an antibiotic. In some embodiments, the efficacy enhancer is chosen from avibactam, tazobactam and clavulanate.

In some embodiments, the antifungals are chosen from imidazoles (such as miconazole, ketoconazole, clotrimazole, econazole, bifonazole, butoconazole, fenticonazole, isoconazole, oxiconazole, sertaconazole, sulconazole, tioconazole, and griseofulvin); triazoles (such as fluconazole, itraconazole, isavuconazole, ravuconazole, posaconazole, voriconazole, and terconazole); thiazoles (such as abafungin); allylamines (such as terbinafine, amorolfine, naftifine, and butenafine); echinocandins (such as echinocandins, anidulafungin, caspofungin, and micafungin); amphotericin B, and azole antifungals. In some embodiments, the antifungal is amphotericin B or nystatin. In some embodiments, the antifungal is terbinafine, aorolfine, or flucytosine. In some embodiments, the antifungal is miconazole or ketoconazole.

In some embodiments, the antifungal is chosen from fluconazole, itraconazole, voriconazole, posaconazole, and ravuconazole.

In some embodiments, the antifungal is chosen from micafungin, caspofungin, and anidulafungin.

In some embodiments, the antifungal is griseofulvin. In some embodiments, the antivirals are chosen from anti-herpetic (antiherpesvirus) agents and anti-influenza agents.

In some embodiments, the anti-herpetic agents are chosen from acyclovir, brivudine, docosanol, famciclovir, idoxuridine, penciclovir, trifluridine, and valacyclovir. In some embodiments, the anti-influenza agents are chosen from amantadine, rimantadine, oseltamivir, and zanamivir.

In some embodiments, the antivirals are chosen from acyclovir, famciclovir, penciclovir, valacyclovir, amantadine, rimantadine, oseltamivir, and zanamivir.

In some embodiments, the pahrmceutical compositions disclosed herein are in a mucosadhesive dosage form.

In some embodiments, viral bacteriophages make it possible to reduce or eliminate colonization and/or infection of humans and animals by pathogenic bacteria, including antibiotic resistant bacteria. Compared to antibiotics, in some embodiments, phages go deeper into the infected area. Antibiotics, on the other hand and in some embodiments, have concentration properties that quickly decrease as they go below the surface of the infection. The replication of phages is concentrated on the infected area where they are needed the most, while antibiotics are metabolized and removed from the body. In addition, secondary resistance does not happen among phages, but happens quite often among antibiotics. Secondary resistance is acquired and occurs when there are not enough blood drug levels. Phages, in some embodiments, provide a good choice for the treatment of drug-resistant bacteria.

In some embodiments, the viral bacteriophages are chosen from phages belonging to a family chosen from ampullaviridae, bicaudaviridae, clavaviridae, corticoviridae, cystoviridae, fuselloviridae, globuloviridae, guttaviridae, inoviridae, leviviridae, microviridae, plasmaviridae, tectiviridae.

In some embodiments, the viral bacteriophages are used as a single phage or in combination (including any other phage belonging to a family chosen from ampullaviridae, bicaudaviridae, clavaviridae, corticoviridae, cystoviridae, fuselloviridae, globuloviridae, guttaviridae, inoviridae, leviviridae, microviridae, plasmaviridae, tectiviridae, and/or others.

In some embodiments, the antihistamines are chosen from azelastine, hydroxyzine, desloratadine, emadastine, levocabastine, azelastine, carbinoxamine, and levocetirizine. In some embodiments, the antihistamines are chosen from fexofenadine, diphenhydramine, dimetane, loratadine, clemastine, chlorpheniramine, and certirizine. In some embodiment, the antihistamines are chosen from brompheniramine, chlorpheniramine, dimenhydrinate, and doxylamine.

In some embodiments, the nasal decongestants are chosen from oxymetazoline, phenylephrine, and pseudoephedrine.

In some embodiments, the active ingredients are chosen from spermicidal agents, prostaglandins, and hormones.

In some embodiments, the pharmaceutical composition is contained on within or embedded within a mucoadhesive polymer. Such polymers are chosen from protein based polymers, polysaccharides, polyesters, polyanhydrides, polyamides, phosphorous based polymers, acrylic polymers, vinylpyrrolidone polymers, celluloses, and silicones.

In some embodiments, the mucoadhesive polymers have a mass average molecular weight above about 75,000 Da to about 20,000,000 Da. In some embodiments, the average molecular weight ranges from about 100,000 to about 20,000,000 Da or from about 200,000 to about 1,000,000 Da or from about 400,000 to about 700,000 Da.

In some embodiments, the mucoadhesive polymers include in general hydrophilic polymers and hydrogels. In the large classes of hydrophilic polymers, those containing carboxylic group exhibit mucoadhesive properties; these include polyvinyl pyrrolidone (PVP), methyl cellulose (MC), sodium carboxy-methylcellulose (SCMC) hydroxypropyl cellulose (HPC) and other cellulose derivative. Hyrogels are the class of polymeric biomaterials that exhibit the basic characteristics of swelling by absorbing water, and then they interact with the mucus that covers epithelium by means of adhesion. Polymers with anionic groups include: carbopol, polyacrylates and their cross-linked modifications, polymers with cationic groups include chitosan and its derivatives and aminoethyl methacrylate or acrylate polymers.

One or more of the following basic properties of a polymer indicate a good mucoadhesive profile: high molecular weight, chain flexibility, high viscosity, optimal cross-linked density of polymer, charge and degree of ionization of polymer (anion>cation>unionized), medium pH, hydration of the polymer, high applied strength and duration of its application and high initial contact time. In addition to the above factors, some physiological factors, like mucin turnover and disease status also affect the mucoadhesion. The mucin turnover is expected to limit the residence time of the mucoadhesive agents on the mucus layer. This could detach mucoadhesives from the surface no matter how high the mucoadhesive strength may be.

In some embodiments, the mucoadhesive system should possess an acceptable active ingredient loading capacity, good mucoadhesion, no irritancy, good feel in the place of administration, sustained drug delivery and an erodible formulation has the added advantage of not requiring retrieval after delivery of the dose. Therefore, hydrophilic polymers with good ability to stick to mucosal membranes are a good chose. They normally possess charged groups or nonionic functional groups capable of forming hydrogen bonds with mucosal surfaces. To accomplish these properties, structural characteristics such as strong hydrogen bonding groups (e.g. carboxyl, hydroxyl, amino- and sulfate groups), strong anionic or cationic charges, high molecular weight, chain flexibility, and surface energy properties favoring spreading onto mucus are sought.

In some embodiments, anionic polymers have demonstrated mucoadhesive properties related to the ability of carboxylic groups to form hydrogen-bonds with oligosaccharide chains of mucins. In some embodiments, weakly anionic carboxyl-containing polymers such as poly(acrylic acid), poly(methacrylic acid), sodium alginate, carboxymethylcellulose and poly(maleic acid)-co-(vinyl methyl ether) are used. In some embodiments, chitosan and some synthetic polymethacrylates are cationic polymers that have mucoadhesiveness. This property has been related to their ability to interact with negatively charged mucins via electrostatic attraction and hydrophobic effects may also play a certain role. In some embodiments, chitosan derivatives relevant to pharmaceutical applications include trimethyl chitosan, glycol chitosan, carboxymethylchitosan and half-acetylated chitosan. In some embodiments, solid micro/nanoparticulate systems based on chitosan and derivatives have been the focus of several studies.

In some embodiments, compared to the charged, non-ionic polymers generally show lesser mucoadhesiveness. The specific interactions between mucin and these kind of polymers are usually very weak. In some embodiments, amphoteric polymers such as gelatin and carboxymethylchitosan, have been explored as mucoadhesive materials for pharmaceutical systems. In some embodiments, their nature of and self-neutralization of cationic and anionic charges within their structure contribute to relatively lesser mucoadhesiveness, similar to non-ionic polymers. In some embodiments, aminated derivative of gelatin has shown a considerable gastric mucoadhesion both in vitro and in vivo in rats.

In some embodiments, polyampholyte polymers displayed particular characteristics that have to be taken into consideration with regarding to their mucoadhesive and penetration-enhancing properties. In some embodiments, they exist positively charged, neutral and negatively charged, depending on dispersion pH and their specific isoelectric point. In some embodiments, the viscosity in the dispersion is minimal and increases when pH is higher or smaller that isoelectric point.

In some embodiments, the presence of inorganic salts affects the viscosity of the dispersion. In some embodiments, the mucoadhesive and penetration enhancing properties of polyampholyte-based formulations are affected by pH-induced structural and physicochemical transformations.

In some embodiments, there is another specific class of polymers called tiomers. They are characterized by containing side chains with thiol-bearing functional groups and are obtained by conjugating conventional mucoadhesive polymers with molecules carrying thiol functionality. The presence of this kind of functional groups enables the formation of disulfide bridges (covalent bonds) with cystein rich sub-domains of mucus glycoproteins either via thiol/disulfide exchange reactions or through a simple oxidation of free thiol groups, exhibiting significantly enhanced mucoadhesive properties in comparison with conventional mucoadhesives. In some embodiments, poly(acrylic acid)/cystein, chitosan/N-acetylcystein, alginate/cystein, chitosan/thioglycolic acid and chitosan/thioethylamidine are typical polymeric thiomers. The development of novel derivatization approaches to thiolate non-ionic polymers may offer a way to improve their poor mucoadhesive performance. In some embodiments, the polymers have acrylate end groups. They are a class of mucoadhesive polymers capable of forming covalent bonds with mucins similar to polymeric thiomers.

In some embodiments, dendrimers have displayed usefulness as mucoadhesives due to their properties and unique structure. In some embodiments, poly(amidoamine) (PAMAM) dendrimers carrying various functional groups (amino, carboxylate and hydroxyl surface groups, COOH) are chosen for mucoadhesiveness. In some embodiments, boronic acid copolymers are chosen for mucoadhesiveness. In some embodiments, copolymers of N-acryloyl-m-aminophenylboronic acid with N,N-dimethylacrylamide (e.g., up to 15 mol-% N-acryloyl-m-aminophenylboronic acid to ensure their solubility in aqueous environment) display interactions with stomach mucin and may facilitate the retention of poly(vinyl alcohol)/borax gels in mucosal lumens, mainly at pH 7.0-9.0, where their complexation with mucins is pronounced.

In some embodiments, polymers containing sugar moieties as pendant groups (synthetic glycopolymers) possess hybrid properties. With this type of material it is possible to easily manipulate the architecture and physicochemical properties, which can be performed through homo- and copolymerization with monomers of different nature.

For example, glycopolymers have been obtained by free-radical copolymerization of N-(2-hydroxypropyl) methacrylamide with various sugar-containing monomers such as N-methacryloylglycylglycylgalactosamine, N-methacryloylglycylglycylfucosylamine, N-methacryloylglycylglycylglucosamine, and N-methacryloylglycylglycylmannosamine. In some embodiments, fucosylamine with copolymers are chosen, e.g., to adhere selectively to the colon in vitro, and stronger adhesion was observed for copolymers containing larger quantities of sugar moieties. The inventors hypothesized that this adhesion is related to the binding of sugar-moieties of the copolymers to specific receptors present in the colonic epithelium. The adhesion of these glycopolymers to the small intestinal mucosa was less pronounced and less sensitive to fucosamine in the copolymers.

In some embodiments, considering the great number of polymers used for developing such systems, one is derived from polyacrylic acid, such as polycarbophil and carbomers; polymers derived from cellulose, such as hydroxyethylcellulose and carboxymethylcellulose; alginates, chitosan and derivatives, lectins and their derivatives are chosen.

In some embodiments, the protein based polymers are chosen from collagens, albumins, and gelatins. In some embodiments, the albumin is conjugated to poly-(ethylene glycol).

In some embodiments, the polysaccharides are chosen from alginates, cyclodextrines, chitosans, dextrans, agarose, hyaluronic acid, starch, and cellulose.

In some embodiments, the polyesters are chosen from poly lactic acid (PLA), polyglycolic acid (PGA), poly lactide-co-glycolide (PLGA), polyhydroxybutyrate (PHB), poly(e-caprolactone), polydioxanone.

In some embodiments, the celluloses are chosen from carboxymethyl cellulose (CMC), methyl cellulose (MC), hydroxyethylcellulose (HEC), hydroxypropyl methyl cellulose (HPMC), hydroxylpropyl cellulose (HFC), ethyl hydroxyethyl cellulose (EHEC), and methyl hydroxyethyl cellulose (MHEC).

In some embodiments, the mucoadhesive polymer has one or more strong hydrogen bonding groups chosen from —OH and —COOH.

In some embodiments, the mucoadhesive polymer is chosen from high molecular weight homo- and copolymers of acrylic acid crosslinked with a polyalkenyl polyether. In some embodiments, the mucoadhesive polymer is chosen from crosslinked acrylic or methacrylic acid based polymers. For example, in some embodiments, the mucoadhesive polymer is chosen from Carbopol or Carbomer brand polymers. For example, in some embodiments, the mucoadhesive polymer is chosen from Carbopol® 934 Polymer, Carbopol® 940 Polymer, Carbopol® 941 Polymer, Carbopol® 980 Polymer, Carbopol® 981 Polymer, Carbopol® 1342 Polymer (Acrylates/C10-30 Alkyl Acrylate Crosspolymer), Carbopol® 1382 Polymer (Acrylates/C10-30 Alkyl Acrylate Crosspolymer), Carbopol® 2984 Polymer, Carbopol® 5984 Polymer, Carbopol® SC-200 Polymer (Acrylates/C10-30 Alkyl Acrylate Crosspolymer, and Carbopol® Silk 100 Polymer. In some embodiments, the mucoadhesive polymer is Carbopol® 940 Polymer.

In some embodiments, the mucoadhesive polymer is chosen from hydroxy propyl cellulose (HPC) or hydroxy propyl methyl cellulose (HPMC).

In some embodiments, the mucoadhesive polymer has an anionic charge.

Another strategy to adjust mucoadhesive properties of the system, is to optimize their mechanical characteristics and modulate their swelling behavior or to improve their biocompatibility to use the polymer blends. New mucoadhesive blends may be obtained by mixture of pharmaceutical polymers in solid state or in solution. When two of these mucoadhesive materials are blended, their mucoadhesive properties are dependent on the strength of specific interactions occurring between both components upon hydration. When there is not the formation of insoluble polycomplexes, the specific interactions between the polymers are not very strong and the mucoadhesiveness of a system will often be intermediate between the adhesiveness of each individual component. Interpolymer complexes such as poly (carboxylic acids) and non-ionic polymers in solutions via hydrogen bonding results in formation of novel polymeric materials-interpolymer complexes. These materials can potentially be used for design of novel mucoadhesive dosage forms.

Preparation of Compounds

Non-bonded amino acids may be purchased from suppliers in a commercial grade with levels of high purity and then added to a volume of liquid. It has been found that it is important to closely control the process steps in combining the various ingredients to form such a complete diet, or various portions thereof, in order to prevent degradation of individual ingredients and/or interactions between ingredients. Thus, after appropriately selecting the levels of amino acids to be employed in the formulation in order to avoid inherently incompatible flavors, as previously indicated, highly pure forms of the amino acids are used. Recrystallizations of individual amino acids are carried out if necessary to insure the absence of undesirable trace contaminants. After proper selection is made and adequate purity is obtained, close control of the process conditions is used to assure ultimate palatability.

In general, certain amino acids are not very water soluble, and such relatively insoluble members are used in the form of the hydrochloride salts and/or esters thereof, which may degrade into their elemental forms. In order to promote the dissolution of the various amino acids in water, the water is usually maintained at a temperature of about 90° C. to 100° C. However, in some embodiments, it has been found that one of the amino acids of the formulation is highly susceptible to thermal degradation to permit its inclusion into the aqueous solution at such temperatures without seriously reducing the efficacy of the liquid dosage form. This ingredient is the non-essential amino acid glutamine. Particular carbohydrates from the group of monosaccharides, disaccharides, starches and dextrins, which may be suitably employed have various degrees of water solubility, and good solubility is desirable in formulating the dosage form.

The non-essential amino acid, aspartic acid, has difficulty with solubility in water even at temperatures in the range of about 90° C. to 100° C. However, it has been found that aspartic acid can be fairly readily dissolved in alkaline water having a pH between about 8 and 14. Thus, the dissolution is facilitated by separately dissolving the aspartic acid in alkaline water having a pH of about 8 or above and then adding this pre-solution to the main solution. In some dosage forms, the pH of a liquid dosage form is from about a pH of 8 to about a pH of 10, but the aspartic acid or salt thereof is stored in alkaline conditions before addition to the solution.

Interactions fairly readily occur at elevated temperature between aldehyde or ketone groups present in the carbohydrate component, such as in glucose. In some embodiments, the solution comprises glucose, (or potential aldehyde groups of a glucose-containing polymer subject to hydrolysis) and the amino acids, particularly lysine. Such interaction results in the formation of condensation products which are brown in color and which have a flavor resembling caramel. In some embodiments methods of making the liquid dosage forms comprise steps taken to minimize the extent of the time-temperature integral over which amino acids and such carbohydrates are both present in the solution in order to thereby minimize the extent of caramelization that may occur. This result is achieved most expeditiously by adding the carbohydrate sufficiently rapidly while agitating the solution to enhance its dissolution. In this respect, the addition of the carbohydrate components, such as glucose, should be sufficiently rapid to drop the temperature to about 40° C. within ten minutes time from the initial addition. It should also be understood that not only does rapid dissolution avoid unpalatability resulting from the interaction between amino acids and the aldehyde or ketone groups of the carbohydrate, but it reduces the time at which the methionine is exposed to the relatively high temperatures. Generally, not all of the carbohydrate is added at this time, although it all could be added at this time if one would so desired, and the remainder is dissolved subsequently in the process.

Although it is considered that the stated formulation has advantages from a cost standpoint and from case of formulation, various minerals may be provided as part of the dosage form in a percentage or trace levels within the solution. Magnesium, for instance, might be provided in the form of acetate, citrate or chloride in some embodiments. Similarly, potassium might be provided in the form of bicarbonate or sorbate. Likewise, iron might be provided in the form of chloride, gluconate, acetate or citrate. Calcium may be supplied as acetate, citrate or bicarbonate. Iodine may be provided as the iodide of sodium, magnesium or manganese. Manganese might be provided as manganous chloride, and zinc could be provided as the acetate. Still other suitable forms may also be used.

In some embodiments, addition to the foregoing minerals, if it is intended to employ the oral or topical dosage form for extended periods of time, metabolizable and nontoxic salts of cobalt and molybdenum are also included. Examples of such suitable salts include sodium, potassium, and ammonium molybdate and cobaltous acetate-$4H_2O$.

The order of addition of these minerals is important in order to avoid potential interactions which might result in precipitates that will adversely affect the solution. Magnesium oxide, which is utilized as the source of magnesium, is readily incorporated into the main solution of essential and non-essential amino acids plus carbohydrate by first being dissolved in an aqueous solution of potassium hydroxide and glucono-delta-lactone to form a pre-solution. The pre-solution in which the magnesium oxide is completely dissolved is slowly added to the main solution.

In some embodiments, hydrated sodium glycerophosphate is added to the solution, as is hydrated ferrous ammonium sulfate. The sodium chloride may also be conveniently added at this time. Following the dissolution of the glycerophosphate and the ferrous compounds, the remainder of the carbohydrate is dissolved in the solution, using constant stirring. The temperature of the solution may be raised slightly in order to expedite the solution of the carbohydrate but the temperature should not exceed 35° C.

At this point which is approaching the end of the dissolution process, the water-soluble vitamins are added, one after another, insuring that each is dissolved before the following one is added. Adding the vitamins earlier and/or while the temperature is higher, is avoided because of the thermal susceptibility of these vitamins, particularly thiamine, for example.

The hydrated calcium chloride is added after the dissolution of the remainder of the carbohydrate. It is extremely important that all of the glycerophosphate compound be completely in solution before the addition of the calcium chloride, and moreover, the addition of the calcium should not immediately follow addition of the glycerophosphate compound because of the potential formation of a refractory precipitate of calcium glycerophosphate. It has been found that such formation of a refractory precipitate is completely avoided if the remainder of the carbohydrate, and preferably also the vitamins, are dissolved in the solution between the initial addition of the glycerophosphate compound and the subsequent dissolution of the soluble calcium compound. It is believed that the glycerophosphate is complexed in some manner by the other ions after a sufficient residence in solution.

In some embodiments, the compositions or pharmaceutical compositions comprise trace amounts of minerals, which can be dissolved in water, and these solutions combined to form one pre-solution. In some methods of making the compositions in solution format, this pre-solution includes the manganous salt, the cupric salt, the zinc salt and the iodide salt, plus the molybdenum and the cobalt salts if such are employed. At this point in the process, the temperature of the main solution is maintained at about 30° C. or below while the pre-solution of the trace minerals is slowly added. Particularly important is the handling of the manganous salt. It has been found that the manganous salt should not be added to the solution prior to the complete dissolution of the water-soluble iron compound, for it appears that a stable solution is not obtained if these two salts are added in the reverse order to a solution containing the amino acids and carbohydrates. It is believed that addition in the reverse order may cause oxidation of the manganous ion to manganese dioxide accompanied by the formation of undesirable precipitates. It is thought that the other ingredients in the solution may well form stable complexes with the ferrous iron if it is added sufficiently prior to the addition of 'the manganous iron, and accordingly the ferrous ion should preferably be dissolved in the solution prior to the second addition of carbohydrate.

Another consideration in making a composition of this type is that the growth of microorganisms, such as bacteria should be prevented. In some embodiments, the solution or liquid dosage form comprises an antibiotic. In some embodiments, the hypertonicity of the solution is controlled such that from the time the temperature is lowered by the first dissolution of the carbohydrate, the amount of water present in the solution, relative to the amount of carbohydrate and solutes, is regulated so that the solution is hypertonic. For purposes of some embodiments, hypertonic solution is defined as having an osmotic pressure higher than that within microorganisms so that undesirable microorganisms, for example, *Escherichia coli*, cannot grow in the solution. The amounts of water added subsequently throughout the process are similarly balanced with the amounts of additional solute so that the hypertonicity of the solution is maintained, at least up to and through the addition of all the water-soluble ingredients.

In some embodiments, the amino acids of the invention comprise a modification on their side chain or N or C terminus. Modification such as a thiol modification, for instance, can be performed by a reaction of introducing a protected or non-protected thiol group at the 3 carbon atom of the amino acid derivative is not particularly limited as long as it is a reaction that introduces a protected or non-protected thiol group at the 3 carbon atom of the amino acid derivative. Introduction may also be carried out after introducing a leaving group at the 0 carbon atom of the amino acid derivative as an exchange reaction with the leaving group.

For example, this reaction can be carried out by reacting the amino acid derivative with a thiol compound. In terms of introducing a protected thiol group, it is preferred to employ a thiol compound having a protecting group and a hydrogen atom bound to the sulfur atom. Thiol compounds can include benzyl mercaptans or tritylthiols that may possess any number of substituents such as a halogen atom such as fluorine, chlorine, bromine, and iodine, an lower alkyl group having 1-4 carbons such as a methyl group and an ethyl group, an alkoxy group having 1-4 carbons such as a methoxy group and an ethoxy group, and a nitro group at any position on the phenyl ring, alkanethiols such as methanethiol, ethanthiol, and t-butanethiol, acyl thiols that can be easily converted into an acetamidomethyl group, a trityl group, and a disulfide group, and the like.

The amount of the thiol compound used may be 1-100 equivalents, preferably 2-20 equivalents, and further preferably 3-10 equivalents to 1 equivalent of the amino acid derivative to be the raw material. Examples of the solvent used can include THF, DCM, DMSO, DMF, and the like, and among these DMF is preferred. The reaction can be carried out in a reaction condition of e.g. at 1-100° C., preferably 10-80° C., and further preferably 15-35° C., for example 30 minutes-24 hours or 3.5 hours-5 hours.

The raw material compound of this reaction may be an amino acid or an amino acid derivative that can have a thiol group introduced at the β-position. In other words, the raw material compound may be an amino acid, or may be an amino acid derivative having the amino group, carboxyl group, side chain substituent, and the like of the amino acid protected or substituted by a substituent. In one aspect, in terms of efficiently carrying out the reaction, it is preferably an amino acid derivative possessing a leaving group at the β-position, and more preferably an amino acid derivative possessing a halogen atom at the β-position. Moreover, in one aspect, in terms of preventing side reactions to increase the yield, it is preferably an amino acid derivative having the amino group and carboxyl group of the amino acid protected.

The reaction of converting the amino group or carboxyl group bound to the α carbon atom of an amino acid derivative into a substituent to be the substrate for a hydrolase selective for D- or L-amino acids is not particularly limited as long as it is a reaction that yields an amino acid derivative having a substituent to be the substrate for a hydrolase selective for D- or L-amino acids bound to the α carbon atom after the reaction. "The amino group or carboxyl group bound to the α carbon atom of an amino acid derivative" in the starting material of the reaction may be a protected or non-protected amino group or carboxyl group. In other words, it may be an unprotected free amino group or carboxyl group, or it may be an amino group or carboxyl group protected by a protecting group. In one aspect, when carrying out this reaction after introducing a thiol group at the 3-position of the amino acid derivative, if an amino acid derivative having a thiol group introduced at the 3-position is used as the raw material and the amino group and carboxyl group are protected for thiolation, the reaction can be carried out using an amino acid derivative having these protected as the raw material.

A group that can be generally employed as the protecting group of the amino group can be employed as the protecting group of the amino group, and e.g. a lipophilic protecting group described below etc. can be employed. For example, in one aspect, examples can include a protecting group such as a 9-fluorenylmethoxycarbonyl (Fmoc) group or a t-butyloxycarbonyl (Boc) group, a carbonate-containing group such as an allyloxy carbonate (Alloc) group, an acyl group such as an acetyl (Ac) group, an aryl group, a benzyl group, and the like. In order to introduce a protecting group, e.g. when introducing a Boc group, this can be carried out by e.g. a method of adding a THF solution of Boc2O to the reaction system. The introduction of the protecting group of the amino group can be carried out with the above method as well as well-known methods according to the protecting group. Moreover, the deprotection of the protecting group of the amino group can be carried out by treatment with an acid or a base. For example, when the protecting group is a Boc group, an acid such as trifluoroacetic acid (TFA) can be used. In doing so, this is preferably carried out in the presence of a solvent, examples of which can include DCM, THF, acetonitrile, and the like. The deprotection of the protecting group of the amino group can be carried out with the above method as well as ordinary methods.

A group that can be generally employed as the protecting group of the carboxyl group can be employed as the protecting group of the carboxyl group, for example a lipophilic protecting group described below etc. can be employed. For example, in one aspect, examples include protection as an ester by an alkyl group such as a methyl group, an ethyl group, and a tert-butyl group, or an arylalkyl group such as a benzyl group. When the protecting group of the carboxyl group is a methyl group, methyl esterification can be carried out e.g. by a method of adding thionyl chloride and methanol. The introduction of the protecting group of the carboxyl group can be carried out with the above method as well as well-known methods depending on the protecting group. Moreover, the deprotection of the protecting group of the carboxyl group can be carried out by treatment with an acid or a base. For example, when the protecting group is a methyl group, a base such as sodium hydroxide can be used. In doing so, this is preferably carried out in the presence of a solvent, examples of which can include THF, dioxane, acetonitrile, and the like. The deprotection of the protecting group of the carboxyl group can be carried out with the above method as well as ordinary methods.

Methods of Using, Methods of Treating and Preventing Infection

In another embodiment of the invention, the composition of the invention is used to treat a patient suffering from, or susceptible to, bacterial infection or fungal infection. In another embodiment of the invention, the composition of the invention is used to treat a patient suffering from, or susceptible to, bacterial infection or fungal infection comprising a biofilm of either or both of one or plurality of bacterial cells in the form of a biofilm or fungal cells in the form of a biofilm. In some embodiments, the compositions or pharmaceutical compositions of the disclosure are used to disrupt a biofilm or biofilms comprising one or a plurality of bacterial cells on the surfaces of a subject or a surface of an inanimate object, such as a laboratory bench, table top, implant (before or after implantation into a subject), or a catheter (before or after fluid communication with a subject is achieved). In some embodiments, the compositions or pharmaceutical compositions of the disclosure are used to disrupt a biofilm or biofilms comprising one or a plurality of fungal cells. In some embodiments, the compositions or pharmaceutical compositions of the disclosure are used to disrupt a biofilm or biofilms comprising one or a plurality of bacterial cells and/or one or a plurality of fungal cells. In some embodiments, the disclosure relates to methods of treating or disputing biofilms derived from bacterial cells and fungal cells. In some embodiments, the disclosure relates to methods of preventing bacterial biofilm formation and/or fungal biofilm formation by administration of any of the pharmaceutical compositions disclosed herein, individually or in combination, to a subject in need thereof in a prophylactically effective amount. In some embodiments, the disclosure relates to methods of simultaneously preventing bacterial biofilm formation and fungal biofilm formation by administration of any of the pharmaceutical compositions disclosed herein, individually or in combination, to a subject in need thereof in a prophylactically effective amount. In some embodiments, the disclosure relates to methods of treating bacterial infection caused by or comprising a bacterial biofilm and/or treating fungal infection caused by or comprising a fungal biofilm by administration of any of the pharmaceutical compositions disclosed herein, individually or in combination, to a subject in need thereof in a therapeutically effective amount. In some embodiments, the disclosure relates to methods of simultaneously treating bacterial biofilm infections and fungal biofilm infections by administration of any of the pharmaceutical compositions disclosed herein in a therapeutically effective amount, individually or in combination (sequentially or simultaneously), to a subject in need thereof.

The disclosure relates to the treatment and/or prevention of fungal infections in a subject caused by fungal cell biofilm formation. In some embodiments, the fungal cells comprise one or a plurality of cells derived from: *Candida albicans, Candida guilliermondii, Candida parapsilosis, Candida glabrata, Candida tropicalis* and/or *Candida* dubliniensis.

The disclosure relates to the treatment and/or prevention of bacterial infections in a subject caused by bacterial biofilm formation. In some embodiments, methods of the disclosure relate method of treatment and/or prevention of bacterial biofilm formation in a subject by administration of a therapeutically or prophylactically effective amount of one or more of the pharmaceutical compositions of the disclosure. In some embodiments, the bacterial cells comprise one or a plurality of cells derived from: *Staphylococcus aureus* (standard wild type and methicillin-resistant strain USA300), *Escherichia coli, Pseudomonas aeruginosa* and/or *Staphylococcus epidermidis*.

In any embodiments of the aforementioned methods, administration may be accomplished by intravenously, topically, irrigation of wounds either as part of a wound dressing or in sterile solution, intradermally, intramucosally, subcutaneously, sublingually, orally, intravaginally, intramuscularly, intracavernously, intarocularly, intranasally, into a sinus, intrarectally, gastrointestinally, intraductally, intrathecally, subdurally, extradurally, intraventricular, intrapulmonary, into an abscess, intra articular, into a bursa, subpericardially, intrauterine, into the plural space, swish and swallow treatment of oral candidiasis, transmucosal, or transdermal administration of the prophylactically or therapeutically effective amount of a composition or pharmaceutical composition disclosed herein to a subject in need thereof. In some embodiments, the method comprises administration of an antibiotic prior to, simultaneously with, or subsequent to administration of the prophylactically or therapeutically effective amount of a composition or pharmaceutical composition disclosed herein to a subject in need thereof. In any of the above methods, the method may comprise administration of an antibiotic or anti-fungal agent intravenously, topically, irrigation of wound either as part of wound dressing or in sterile solution, intradermaly, submucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abcess, intra articular, into a bursa, subpericardially, intrauterine, into the plural space, into the peritoneal cavity, swish and swallow treatment of oral candidiasis, for transmucosal, or for transdermal administration.

If, for instance, the pharmaceutical compositions are administered intracavernously, the pharmaceutical compositions comprise, in some embodiments, a pharmaceutically effective amount of one of the compositions disclosed herein and a pharmaceutically acceptable carrier which may be in solution form and contacted with a wound or in a solution or solid form as part of a wound dressing. The wound dressing may be physically applied in contact to a wound or the skin. In some embodiments, the pharmaceutical compositions are administered as a mouth wash or rinse that is designed not to be ingested but rather swished and spit out.

The pharmaceutical compositions of the disclosure can be topically administered in any formulation, including a gel or liquid solution. A sufficient amount of the topical preparation can be gently rubbed onto the affected area and surrounding skin, for example, in an amount sufficient to cover an affected area plus a margin of healthy skin or tissue surrounding the affected area, for example, a margin of about 0.5 inches. The compositions can be applied to any surface of the body, including for example, skin, scalp, face, eyebrows, eyelashes, bearded areas, nail surface, nail bed, nail matrix, and nail fold, as well as to the mouth, vagina, eye, nose, or other mucous membranes.

In some superficial fungal infections of the skin, the composition is applied in a single application four times a day to once a month or, once a week, once a bi-week, once a month, or from one to four times daily, for a period of time sufficient to alleviate signs and/or symptoms or clear the fungal infection. For example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. The present compositions can be administered, for example, at a frequency of once per day or twice per day. The presently described compositions can be topically administered once per day for a period of time from 1 week to 8 weeks, from 1 week to 4 weeks, for 1 week, for 2 weeks, for 3 weeks, for 4 weeks, for 5 weeks, for 6 weeks, for 7 weeks, or for 8 weeks.

The presently described compositions can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24-hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

For example, generally for *Tinea corporis, Tinea cruris* or *Tinea faciei*, the present composition can be applied, for example once or twice daily, for example, morning and evening, for about 2-4 weeks. Generally for *Tinea pedis* application the present composition can be applied once daily, for 2 weeks or longer.

For example, the presently described compositions can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

In some embodiments, for onychomycosis infections, the compositions are applied at a frequency of from one to four times daily, for a period of six weeks for infections of the fingernails or twelve weeks for infection of the toenails. This treatment may be repeated including for example, once daily, twice daily, three times daily, or four times daily, one a daily or weekly basis, or on a monthly or every other month schedule, for a period of time sufficient to alleviate symptoms or clear the fungal infection, for example, for a period of time from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, for 50 weeks, or for 52 weeks. For example, the present compositions can be topically administered, at a frequency of once per day for a period of time from 1 week to 52 weeks, for example for about from 24 weeks to 48 weeks.

In some embodiments, for onychomycosis infections the compositions are applied in a therapeutically effective amount, for example, an amount sufficient to cover an affected area plus a margin of healthy skin and/or nail surrounding the affected area, for example, a margin of about 0.1 to about 0.5 inches. Suitable amounts per application per affected area or cumulative daily dosage per affected area is applied.

In certain onychomycosis cases a maximum per application, per affected area, dose of 8 grams of the presently described composition is applied to an affected area (all nails), for example, once or twice daily. In some embodiments, the present composition is applied, for example once or twice daily, for example, morning and/or evening, for about 1-52 weeks. For example, in some embodiments, the presently described compositions are topically applied in an amount sufficient to cover an affected area plus a margin of healthy skin and/or nail surrounding the affected area, for example, a margin of about 0.1 to about 0.5 inches, at a frequency, for example, of once a day, for a time period, for example of about 24 to about 48 weeks.

In some embodiments, the pharmaceutical composition is free of glucose. In some embodiments, the pharmaceutical composition is free of glucose at about 5% weight to volume in liquid formulation.

Also, this/these amino acid(s) could be used topically used on humans and also used for sterilizing surgical equipment in solid or liquid surfaces that need be kept free of biofilm producing bacteria and fungi. (one or more nails and, for example, one or two applications in a 24-hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In some embodiments, the pharmaceutical compositions are given in a single or multiple doses per time period, for example, daily, weekly, bi-weekly, or monthly. For example, in some embodiments, the pharmaceutical compositions are given from one to four times per period.

In some embodiments, for superficial fungal infections of the skin, the present compositions are given once per week, for a period of from one to six weeks.

Two commercially available amino acid solutions that are used for intravenous administration and are approved by the food and drug administration (FDA) for this use; PROCALAMINE® (B Braun Medical, Inc.) and AMINOSYN® (Hospira, Inc.) were evaluated. PROCALAMINE® and AMINOSYN® have a similar composition of amino acids except that PROCALAMINE® has cysteine that is missing from AMINOSYN® and AMINOSYN® has three additional amino acids: tyrosine, which has been found to have a neutral effect on biofilms, whereas the additional two amino acids aspartic acid and glutamic acid, were found to be very active against biofilms. Both solutions were compared for their abilities to inhibit and disrupt bacterial and fungal biofilms. PROCALAMINE® was found to be superior. The only other difference between the two solutions was the carbohydrate used in these solutions. PROCALAMINE® used 3% glycerol whereas AMINOSYN® does not; AMINOSYN® can be administered to patients with the addition of 5-10% dextrose (glucose). While glycerol on its own was not found to have antibiofilm effects, there may be an effect that enables the antibiofilm amino acids to be more effective in combating the biofilm in the presence of glycerol. For example, when the biofilm takes up glycerol at any concentration as a source of energy, it may make it more vulnerable to the antagonistic antibiofilm action of amino acids. PROCALAMINE® is a 3% amino acid and 3% glycerin injection with electrolytes containing 3.0 g glycerin, essential amino acids (i.e., 0.21 g L-isoleucine, 0.27 g L-leucine, 0.22 g L-lysine, 0.16 g methionine, 0.17 g L-phenylalanine, 0.12 g L-threonine, 0.046 g L-tryptophan, and 0.20 g L-valine), nonessential amino acids (i.e., 0.21 g L-alanine, 0.42 g glycine, 0.29 g L-arginine, 0.085 g L-histidine, 0.35 g L-proline, 0.18 g L-serine, and 0.014 g L-cysteine), 0.20 g sodium acetate-3H$_2$O, 0.054 g magnesium acetate-4H$_2$O, 0.026 g calcium acetate-H$_2$O, 0.12 g sodium chloride, and 0.15 g potassium chloride. AMINOSYN® II 3.5% contains (per 100 mL) essential amino acids (i.e., 462 mg isoleucine, 700 mg leucine, 735 mg lysine acetate, 120 mg methionine, 209 mg phenylalanine, 280 mg threonine, 140 mg tryptophan, and 350 mg valine), nonessential amino acids (i.e., 695 mg alanine, 713 mg arginine, 490 mg L-aspartic acid, 517 mg L-glutamic acid, 210 mg histidine, 505 mg proline, 371 mg serine, 189 mg N-acetyl-L-tyrosine, and 360 mg glycine), 36 mEq/liter sodium, 50.3 mEq/liter aceate, and 60.0 mEq/liter sodium hydrosulfite. Two other AMINOSYN® formulations are available, including 7% with electrolytes and 8.5% with electrolytes.

In animal species other than *Homo sapiens*, amino acids may be present in their blood other than the 34 that were examined for this patent. These different amino acids would be examined for effect on bacterial and fungal biofilm, then used in a species specific way and could be used on instruments and surfaces to combat bacterial and fungal organisms that produce biofilm.

Other amino acids in the blood of animals (not examined herein) could combat bacterial and fungal biofilm and therefore may be useful in treating these bacterial and fungal infections that would lie on the external surfaces of infected animals such as humans and could also be used to combat these pathogens on instruments and surfaces that need to be treated.

EMBODIMENTS 1-60

Embodiment 1

A composition comprising: (a) non-bonded beta-alanine, or a pharmaceutically acceptable salt thereof, at a weight to volume percent from about 0.1% to about 5.0%; (b) non-bonded 2-aminoadipic acid, or a pharmaceutically acceptable salt thereof, at a weight to volume percent from about 0.1% to about 5.0%; (c) non-bonded aspartic acid, or a pharmaceutically acceptable salt thereof, at a weight to volume percent from about 0.1% to about 5.0%; (d) non-bonded cystathionine (0.2%), or a pharmaceutically acceptable salt thereof, at a weight to volume percent from about 0.1% to about 5.0%; (e) non-bonded cysteine, or a pharmaceutically acceptable salt thereof, at a weight to volume percent from about 0.1% to about 5.0%; (f) non-bonded ethanolamine, or a pharmaceutically acceptable salt thereof, at a weight to volume percent from about 0.1% to about 5.0%; (g) non-bonded glutamic acid, or a pharmaceutically acceptable salt thereof, at a weight to volume percent from about 0.1% to about 5.0%, (h) non-bonded homocysteine, or a pharmaceutically acceptable salt thereof, at a weight to volume percent from about 0.1% to about 5.0%; (i) non-bonded hydroxyproline, or a pharmaceutically acceptable salt thereof, at a weight to volume percent from about 0.1% to about 5.0%; (j) non-bonded phosphoethanolamine, or a pharmaceutically acceptable salt thereof, at a weight to volume percent from about 0.1% to about 5.0%; (j) non-bonded phosphoserine, or a pharmaceutically acceptable salt thereof, at a weight to volume percent from about 0.1% to about 5.0%; or (k) a combination of two or more of (a), (b), (c), (d), (e), (f), (g), (h), (i), and (j).

Embodiment 2

A composition comprising: (a) non-bonded beta-alanine or a pharmaceutically acceptable salt thereof; (b) non-bonded 2-aminoadipic acid or a pharmaceutically acceptable salt thereof; (c) non-bonded aspartic acid or a pharmaceutically acceptable salt thereof; (d) non-bonded cystathionine or a pharmaceutically acceptable salt thereof; (e) non-bonded cysteine or a pharmaceutically acceptable salt thereof, (f) non-bonded ethanolamine or a pharmaceutically acceptable salt thereof; (g) non-bonded glutamic acid or a pharmaceutically acceptable salt thereof, (h) non-bonded homocysteine or a pharmaceutically acceptable salt thereof, (i) non-bonded hydroxyproline or a pharmaceutically acceptable salt thereof, (j) non-bonded phosphoethanolamine or a pharmaceutically acceptable salt thereof, (j) non-bonded phosphoserine or a pharmaceutically acceptable salt thereof, or (k) a combination of two or more of (a), (b), (c), (d), (e), (f), (g), (h), (i), and (j).

Embodiment 3

The composition of Embodiment 1 or 2, comprising (c).

Embodiment 4

The composition of Embodiment 1 or 2, comprising (e).

Embodiment 5

The composition of Embodiment 1 or 2, comprising (g).

Embodiment 6

The composition of Embodiment 1 or 2, comprising (c) and (e).

Embodiment 7

The composition of Embodiment 1 or 2, comprising (c) and (g).

Embodiment 8

The composition of Embodiment 1 or 2, comprising (e) and (g).

Embodiment 9

The composition of Embodiment 1 or 2, comprising (c), (e), and (g).

Embodiment 10

The composition of Embodiment 9, wherein (c) is at a weight to volume percent of about 0.4% to about 0.6%; (e) is at a weight to volume percent of about 0.4% to about 0.6%; and (g) is at a weight to volume percent of about 0.4% to about 0.6%.

Embodiment 11

The composition of Embodiment 9 or 10, wherein (c) is L-aspartic acid; (e) is L-cysteine; and (g) is L-glutamic acid.

Embodiment 12

The composition of Embodiment 9, wherein (c) is L-aspartic acid at a weight to volume percent of about 0.5%; (e) is L-cysteine at a weight to volume percent of about 0.5%; and (g) is L-glutamic acid at a weight to volume percent of about 0.5%.

Embodiment 13

The composition of Embodiment 9, wherein (c) is L-aspartic acid at a weight to volume percent of about 0.4%; (e) is L-cysteine at a weight to volume percent of about 0.4%; and (g) is L-glutamic acid at a weight to volume percent of about 0.4%.

Embodiment 14

The composition of Embodiment 9, wherein (c) is L-aspartic acid at a weight to volume percent of about 2%; (e) is L-cysteine at a weight to volume percent of about 2%; and (g) is L-glutamic acid at a weight to volume percent of about 2%.

Embodiment 15

The composition of Embodiment 1 or 2, comprising (a), (b), (c), (d), (e), (f), (g), (h), (i), and (j).

Embodiment 16

The composition of Embodiment 1 or 2, comprising two of (a), (b), (c), (d), (e), (f), (g), (h), (i), and (j).

Embodiment 17

The composition of Embodiment 1 or 2, comprising three of (a), (b), (c), (d), (e), (f), (g), (h), (i), and (j).

Embodiment 18

The composition of Embodiment 1 or 2, comprising four of (a), (b), (c), (d), (e), (f), (g), (h), (i), and (j).

Embodiment 19

The composition of Embodiment 1 or 2, comprising five of (a), (b), (c), (d), (e), (f), (g), (h), (i), and (j).

Embodiment 20

The composition of Embodiment 1 or 2, comprising six of (a), (b), (c), (d), (e), (f), (g), (h), (i), and (j).

Embodiment 21

The composition of Embodiment 1 or 2, comprising seven of (a), (b), (c), (d), (e), (f), (g), (h), (i), and (j).

Embodiment 22

The composition of Embodiment 1 or 2, comprising eight of (a), (b), (c), (d), (e), (f), (g), (h), (i), and (j).

Embodiment 23

The composition of Embodiment 1 or 2, comprising nine of (a), (b), (c), (d), (e), (f), (g), (h), (i), and (j).

Embodiment 24

The composition of any one of Embodiments 1 to 23, wherein the composition is free of non-bonded tyrosine or a salt thereof.

Embodiment 25

The composition of any one of Embodiments 1 to 24, wherein the composition is free of non-bonded phenylalanine or a pharmaceutically acceptable salt thereof, at a weight percent from about 0.5% to about 4.0%.

Embodiment 26

The composition of any one of Embodiments 1 to 25, wherein the composition is free of non-bonded valine or a pharmaceutically acceptable salt thereof at a weight percent from about 0.5% to about 4.0%.

Embodiment 27

The composition of any one of Embodiments 1 to 26, wherein the composition is free of non-bonded arginine, or a pharmaceutically acceptable salt thereof, at a weight percent from about 0.5% to about 4.0%.

Embodiment 28

The composition of any one of Embodiments 1 to 27, wherein the composition is free of non-bonded methionine, or a pharmaceutically acceptable salt thereof, at a weight percent from about 0.5% to about 4.0%.

Embodiment 29

The composition of any one of Embodiments 1 to 28, wherein the composition is free of non-bonded serine, or a pharmaceutically acceptable salt thereof, at a weight percent from about 0.5% to about 4.0%.

Embodiment 30

The composition of any one of Embodiments 1 to 29, wherein the composition is free of non-bonded threonine, or a pharmaceutically acceptable salt thereof, at a weight percent from about 0.5% to about 4.0%.

Embodiment 31

The composition of any one of Embodiments 1 to 30, wherein the composition is free of non-bonded leucine, or a pharmaceutically acceptable salt thereof, at a weight percent from about 0.5% to about 4.0%.

Embodiment 32

The composition of any one of Embodiments 1 to 31, wherein the composition is free of non-bonded isoleucine, or a pharmaceutically acceptable salt thereof, at a weight percent from about 0.5% to about 4.0%.

Embodiment 33

The composition of any one of Embodiments 1 to 32, wherein the composition is free of non-bonded citrulline, or a pharmaceutically acceptable salt thereof, at a weight percent from about 0.5% to about 4.0%.

Embodiment 34

The composition of any one of Embodiments 1 to 33, wherein the composition is free of non-bonded alanine, or a pharmaceutically acceptable salt thereof, at a weight percent from about 0.5% to about 4.0%.

Embodiment 36

The composition of any one of Embodiments 1 to 34, wherein the composition is free of non-bonded asparagine, or a pharmaceutically acceptable salt thereof, at a weight percent from about 0.5% to about 4.0%.

Embodiment 36

The composition of any one of Embodiments 1 to 35, wherein the composition is free of non-bonded glycine, or a pharmaceutically acceptable salt thereof, at a weight percent from about 0.5% to about 4.0%.

Embodiment 37

The composition of any one of Embodiments 1 to 36, wherein the composition is free of non-bonded taurine, or a pharmaceutically acceptable salt thereof, at a weight percent from about 0.5% to about 4.0%.

Embodiment 38

The composition of any one of Embodiments 1 to 37, wherein the composition is free of non-bonded tryptophan, or a pharmaceutically acceptable salt thereof, at a weight percent from about 0.5% to about 4.0%.

Embodiment 39

The composition of any one of Embodiments 1 to 38, wherein the composition is free of non-bonded cystathione, or a pharmaceutically acceptable salt thereof, at a weight percent from about 0.5% to about 4.0%.

Embodiment 40

The composition of any one of Embodiments 1 to 39, wherein the composition is free of non-bonded 1-methyl-histidine, or a pharmaceutically acceptable salt thereof, at a weight percent from about 0.5% to about 4.0%.

Embodiment 41

The composition of any one of Embodiments 1 to 40, wherein the composition is free of non-bonded 2 aminobutyric acid, or a pharmaceutically acceptable salt thereof, at a weight percent from about 0.5% to about 4.0%.

Embodiment 42

The composition of any one of Embodiments 1 to 41, wherein the composition is free of non-bonded glutamine, or a pharmaceutically acceptable salt thereof, at a weight percent from about 0.5% to about 4.0%.

Embodiment 43

The composition of any one of Embodiments 1 to 42, wherein the composition is free of non-bonded histidine, or a pharmaceutically acceptable salt thereof, at a weight percent from about 0.5% to about 4.0%.

Embodiment 44

The composition of any one of Embodiments 1 to 43, wherein the composition is free of non-bonded ornithine, or a pharmaceutically acceptable salt thereof, at a weight percent from about 0.5% to about 4.0%.

Embodiment 45

The composition of any one of Embodiments 1 to 44, wherein the composition is free of non-bonded lysine, or a pharmaceutically acceptable salt thereof, at a weight percent from about 0.5% to about 4.0%.

Embodiment 46

The composition of any one of Embodiments 1 to 45, wherein the composition is free of one or more of: non-bonded alanine or salt thereof, non-bonded arginine or a salt thereof, non-bonded asparagine or a salt thereof, non-bonded citrulline or a salt thereof, non-bonded glycine or a salt thereof, non-bonded isoleucine or a salt thereof, non-bonded leucine or a salt thereof, non-bonded lysine or a salt thereof, non-bonded methionine or a salt thereof, non-bonded 3-methylhistidine or a salt thereof, non-bonded phenylalanine or a salt thereof, non-bonded ornithine or a salt thereof, non-bonded proline or a salt thereof, non-bonded serine or a salt thereof, non-bonded taurine or a salt thereof, non-bonded threonine or a salt thereof, non-bonded tryptophan or a salt thereof, and non-bonded valine or a salt thereof.

Embodiment 47

A pharmaceutical composition comprising the composition of any one of Embodiments 1 to 46 and a pharmaceutically acceptable carrier.

Embodiment 48

The pharmaceutical composition of Embodiment 47, wherein the pharmaceutically acceptable carrier is sterile saline.

Embodiment 49

A method of disrupting a fungal biofilm, a bacterial biofilm, or a fungal biofilm and a bacterial biofilm, the method comprising contacting the biofilm with the composition of any of Embodiments 1 to 46 or the pharmaceutical composition of Embodiment 47 or 48.

Embodiment 50

A method of treating and/or preventing a fungal infection and/or formation of a fungal biofilm in a subject in need, the method comprising administering to the subject the composition of any of Embodiments 1 to 46 or the pharmaceutical composition of Embodiment 47 or 48.

Embodiment 54

A method of treating and/or preventing a bacterial infection and/or formation of a bacterial biofilm in a subject in need thereof, the method comprising administering to the subject the composition of any of Embodiments 1 to 46 or the pharmaceutical composition of Embodiment 47 or 48.

Embodiment 52

The method of any one of Embodiments 49 to 51, comprising administering the composition or pharmaceutical composition intravenously, topically, via wound irrigation (for example wound dressing or sterile solution), intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment, transmucosally, or transdermally.

Embodiment 53

The method of any one of Embodiments 49 to 52, wherein the infection comprises *Candida albicans, Candida guilliermondii, Candida parapsilosis, Candida glabrata, Candida tropicalis, Candida dubliniensis, Staphylococcus aureus, Escherichia coli, Pseudomonas aeruginosa, Staphylococcus epidermidis*, or a combination of two or more thereof.

Embodiment 54

The method of any one of Embodiments 49 to 53, wherein the infection comprises *Candida albicans, Candida guilliermondii, Candida parapsilosis, Candida glabrata, Candida tropicalis, Candida* dubliniensis, or a combination of two or more thereof.

Embodiment 55

The method of any of Embodiments 49 to 54, comprising topically administering the composition or pharmaceutical composition by irrigation.

Embodiment 56

The method of any of Embodiment 49, wherein disrupting comprises contacting the composition or pharmaceutical composition with a biofilm in or on a catheter or in fluid communication with an animal or prior to attachment of the catheter for fluid communication in an animal.

Embodiment 57

A method of sterilizing an implant or biomedical device, optionally in fluid communication with a subject's circulatory system, the method comprising contacting a surface of the implant or a surface of the biomedical device with an effective amount of the composition of any one of Embodiments 1 to 46 or the pharmaceutical composition of Embodiment 47 or 48.

Embodiment 58

The method of Embodiment 57, wherein the biomedical device is a catheter or tube in fluid communication with the subject a subject's circulatory system.

Embodiment 59

A method of preventing formation of a biofilm and/or disrupting an existing biofilm on a surface, the method comprising contacting the surface with an effective amount of the composition of any one of Embodiments 1 to 46 or the pharmaceutical composition of Embodiment 47 or 48.

Embodiment 60

The composition of any one of Embodiments 1 to 46, further comprising glycerin at a weight to volume percentage of from about 0.1% to about 5.0%.

EMBODIMENTS A1-A40

Embodiment A1

A composition comprising about 0.5% L-cysteine, about 0.5% L-glutamic acid, and about 0.5% L-aspartic acid.

Embodiment A2

A composition comprising about 0.4% L-cysteine, about 0.4% L-glutamic acid, and about 0.4% L-aspartic acid.

Embodiment A3

A composition comprising about 0.3% L-cysteine, about 0.3% L-glutamic acid, and about 0.3% L-aspartic acid.

Embodiment A4

A composition comprising about 0.2% L-cysteine, about 0.2% L-glutamic acid, and about 0.2% L-aspartic acid.

Embodiment A5

A composition comprising about 0.1% L-cysteine, about 0.1% L-glutamic acid, and about 0.1% L-aspartic acid.

Embodiment A6

A composition comprising about 0.6% L-cysteine, about 0.6% L-glutamic acid, and about 0.6% L-aspartic acid.

Embodiment A7

A composition comprising about 0.7% L-cysteine, about 0.7% L-glutamic acid, and about 0.7% L-aspartic acid.

Embodiment A8

A composition comprising about 0.8% L-cysteine, about 0.8% L-glutamic acid, and about 0.8% L-aspartic acid.

Embodiment A9

A composition comprising about 0.9% L-cysteine, about 0.9% L-glutamic acid, and about 0.9% L-aspartic acid.

Embodiment A10

A composition comprising about 1% L-cysteine, about 1% L-glutamic acid, and about 1% L-aspartic acid.

Embodiment A11

A composition comprising from about 0.49% to about 0.51% L-cysteine, from about 0.49% to about 0.51% L-glutamic acid, and from about 0.49% to about 0.51% L-aspartic acid.

Embodiment A12

A composition comprising from about 0.48% to about 0.52% L-cysteine, from about 0.48% to about 0.52% L-glutamic acid, and from about 0.48% to about 0.52% L-aspartic acid.

Embodiment A13

A composition comprising from about 0.47% to about 0.53% L-cysteine, from about 0.47% to about 0.53% L-glutamic acid, and from about 0.47% to about 0.53% L-aspartic acid.

Embodiment A14

A composition comprising from about 0.46% to about 0.54% L-cysteine, from about 0.46% to about 0.54% L-glutamic acid, and from about 0.46% to about 0.54% L-aspartic acid.

Embodiment A15

A composition comprising from about 0.45% to about 0.55% L-cysteine, from about 0.45% to about 0.55% L-glutamic acid, and from about 0.45% to about 0.55% L-aspartic acid.

Embodiment A16

A composition comprising from about 0.44% to about 0.56% L-cysteine, from about 0.44% to about 0.56% L-glutamic acid, and from about 0.44% to about 0.56% L-aspartic acid.

Embodiment A17

A composition comprising from about 0.43% to about 0.57% L-cysteine, from about 0.43% to about 0.57% L-glutamic acid, and from about 0.43% to about 0.57% L-aspartic acid.

Embodiment A18

A composition comprising from about 0.42% to about 0.58% L-cysteine, from about 0.42% to about 0.58% L-glutamic acid, and from about 0.42% to about 0.58% L-aspartic acid.

Embodiment A19

A composition comprising from about 0.41% to about 0.59% L-cysteine, from about 0.41% to about 0.59% L-glutamic acid, and from about 0.41% to about 0.59% L-aspartic acid.

Embodiment A20

A composition comprising from about 0.4% to about 0.6% L-cysteine, from about 0.4% to about 0.6% L-glutamic acid, and from about 0.4% to about 0.6% L-aspartic acid.

Embodiment A21

A composition comprising from about 0.35% to about 0.65% L-cysteine, from about 0.35% to about 0.65% L-glutamic acid, and from about 0.35% to about 0.65% L-aspartic acid.

Embodiment A22

A composition comprising from about 0.3% to about 0.7% L-cysteine, from about 0.3% to about 0.7% L-glutamic acid, and from about 0.3% to about 0.7% L-aspartic acid.

Embodiment A23

A composition comprising from about 0.25% to about 0.75% L-cysteine, from about 0.25% to about 0.75% L-glutamic acid, and from about 0.25% to about 0.75% L-aspartic acid.

Embodiment A24

A composition comprising from about 0.2% to about 0.8% L-cysteine, from about 0.2% to about 0.8% L-glutamic acid, and from about 0.2% to about 0.8% L-aspartic acid.

Embodiment A25

A composition comprising from about 0.15% to about 0.85% L-cysteine, from about 0.15% to about 0.85% L-glutamic acid, and from about 0.15% to about 0.85% L-aspartic acid.

Embodiment A26

A composition comprising from about 0.1% to about 0.9% L-cysteine, from about 1% to about 0.9% L-glutamic acid, and from about 0.1% to about 0.9% L-aspartic acid.

Embodiment A27

A composition comprising from about 0.1% to about 1% L-cysteine, from about 0.1% to about 1% L-glutamic acid, and from about 0.1% to about 1% L-aspartic acid.

Embodiment A28

A pharmaceutical composition comprising the composition of any one of Embodiments A1 to A27 and a pharmaceutically acceptable carrier.

Embodiment A29

The pharmaceutical composition of Embodiment A28, wherein the pharmaceutically acceptable carrier is sterile saline.

Embodiment A30

A method of disrupting a fungal biofilm, a bacterial biofilm, or a fungal biofilm and a bacterial biofilm, the method comprising contacting the biofilm with the composition of any of Embodiments A1 to A27 or the pharmaceutical composition of Embodiment A28 or A29.

Embodiment A31

A method of treating and/or preventing a fungal infection and/or formation of a fungal biofilm in a subject in need, the method comprising administering to the subject the composition of any of Embodiments A1 to A27 or the pharmaceutical composition of Embodiment A28 or A29.

Embodiment A32

A method of treating and/or preventing a bacterial infection and/or formation of a bacterial biofilm in a subject in need thereof, the method comprising administering to the subject the composition of any of Embodiments A1 to A27 or the pharmaceutical composition of Embodiment A28 or A29.

Embodiment A33

The method of any one of Embodiments A30 to A32, comprising administering the composition or pharmaceutical composition intravenously, topically, via wound irrigation (for example wound dressing or sterile solution), intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment, transmucosally, or transdermally.

Embodiment A34

The method of any one of Embodiments A30 to A33, wherein the infection comprises *Candida albicans, Candida guilliermondii, Candida parapsilosis, Candida glabrata, Candida tropicalis, Candida dubliniensis, Staphylococcus aureus, Escherichia coli, Pseudomonas aeruginosa, Staphylococcus epidermidis*, or a combination of two or more thereof.

Embodiment A35

The method of any one of Embodiments A30 to A34, wherein the infection comprises *Candida albicans, Candida guilliermondii, Candida parapsilosis, Candida glabrata, Candida tropicalis, Candida* dubliniensis, or a combination of two or more thereof. Embodiment A36. The method of any of Embodiments A30 to A35, comprising topically administering the composition or pharmaceutical composition by irrigation.

Embodiment A37

The method of any of Embodiment A30, wherein disrupting comprises contacting the composition or pharmaceutical composition with a biofilm in or on a catheter or in fluid communication with an animal or prior to attachment of the catheter for fluid communication in an animal.

Embodiment A38

A method of sterilizing an implant or biomedical device, optionally in fluid communication with a subject's circulatory system, the method comprising contacting a surface of the implant or a surface of the biomedical device with an effective amount of the composition of any one of Embodiments A1 to A27 or the pharmaceutical composition of Embodiment A28 or A29.

Embodiment A39

The method of Embodiment A38, wherein the biomedical device is a catheter or tube in fluid communication with the subject a subject's circulatory system.

Embodiment A40

A method of preventing formation of a biofilm and/or disrupting an existing biofilm on a surface, the method comprising contacting the surface with an effective amount of the composition of any one of Embodiments A1 to A27 or the pharmaceutical composition of Embodiment A28 or A29.

EMBODIMENTS N1-N67

Embodiment N1

A composition comprising about 0.5% L-cysteine, about 0.5% L-glutamic acid, and about 0.5% L-aspartic acid.

Embodiment N2

A composition comprising about 0.4% L-cysteine, about 0.4% L-glutamic acid, and about 0.4% L-aspartic acid.

Embodiment N3

A composition comprising about 0.2% L-cysteine, about 0.2% L-glutamic acid, and about 0.2% L-aspartic acid.

Embodiment N4

A composition comprising: (a) non-bonded beta-alanine, or a pharmaceutically acceptable salt thereof, at a weight to volume percent from about 0.1% to about 5.0%; (b) non-bonded 2-aminoadipic acid, or a pharmaceutically acceptable salt thereof, at a weight to volume percent from about 0.1% to about 5.0%; (c) non-bonded aspartic acid, or a pharmaceutically acceptable salt thereof, at a weight to volume percent from about 0.1% to about 5.0%; (d) non-bonded cystathionine (0.2%), or a pharmaceutically acceptable salt thereof, at a weight to volume percent from about 0.1% to about 5.0%; (e) non-bonded cysteine, or a pharmaceutically acceptable salt thereof, at a weight to volume percent from about 0.1% to about 5.0%; (f) non-bonded ethanolamine, or a pharmaceutically acceptable salt thereof, at a weight to volume percent from about 0.1% to about 5.0%; (g) non-bonded glutamic acid, or a pharmaceutically acceptable salt thereof, at a weight to volume percent from about 0.1% to about 5.0%, (h) non-bonded homocysteine, or a pharmaceutically acceptable salt thereof, at a weight to volume percent from about 0.1% to about 5.0%; (i) non-bonded hydroxyproline, or a pharmaceutically acceptable salt thereof, at a weight to volume percent from about 0.1% to about 5.0%; (j) non-bonded phosphoethanolamine, or a pharmaceutically acceptable salt thereof, at a weight to volume percent from about 0.1% to about 5.0%; (j) non-bonded phosphoserine, or a pharmaceutically acceptable salt thereof, at a weight to volume percent from about 0.1% to about 5.0%; or (k) a combination of two or more of (a), (b), (c), (d), (e), (f), (g), (h), (i), and (j).

Embodiment N5

A composition comprising: (a) non-bonded beta-alanine or a pharmaceutically acceptable salt thereof; (b) non-bonded 2-aminoadipic acid or a pharmaceutically acceptable salt thereof; (c) non-bonded aspartic acid or a pharmaceutically acceptable salt thereof; (d) non-bonded cystathionine or a pharmaceutically acceptable salt thereof; (e) non-bonded cysteine or a pharmaceutically acceptable salt thereof; (f) non-bonded ethanolamine or a pharmaceutically acceptable salt thereof; (g) non-bonded glutamic acid or a pharmaceutically acceptable salt thereof; (h) non-bonded homocysteine or a pharmaceutically acceptable salt thereof; (i) non-bonded hydroxyproline or a pharmaceutically acceptable salt thereof; (j) non-bonded phosphoethanolamine or a pharmaceutically acceptable salt thereof; (j) non-bonded phosphoserine or a pharmaceutically acceptable salt thereof; or (k) a combination of two or more of (a), (b), (c), (d), (e), (f), (g), (h), (i), and (j).

Embodiment N6

The composition of Embodiment N4 or N5, comprising (c).

Embodiment N7

The composition of Embodiment N4 or N5, comprising (e).

Embodiment N8

The composition of Embodiment N4 or N5, comprising (g).

Embodiment N9

The composition of Embodiment N4 or N5, comprising (c) and (e).

Embodiment N10

The composition of Embodiment N4 or N5, comprising (c) and (g).

Embodiment N11

The composition of Embodiment N4 or N5, comprising (e) and (g).

Embodiment N12

The composition of Embodiment N4 or N5, comprising (c), (e), and (g).

Embodiment N13

The composition of Embodiment N12, wherein (c) is at a weight to volume percent of about 0.4% to about 0.6%; (e) is at a weight to volume percent of about 0.4% to about 0.6%; and (g) is at a weight to volume percent of about 0.4% to about 0.6%.

Embodiment N14

The composition of Embodiment N12 or N13, wherein (c) is L-aspartic acid; (e) is L-cysteine; and (g) is L-glutamic acid.

Embodiment N15

The composition of Embodiment N12, wherein (c) is L-aspartic acid at a weight to volume percent of about 0.5%; (e) is L-cysteine at a weight to volume percent of about 0.5%; and (g) is L-glutamic acid at a weight to volume percent of about 0.5%.

Embodiment N16

The composition of Embodiment N12, wherein (c) is L-aspartic acid at a weight to volume percent of about 0.4%;

(e) is L-cysteine at a weight to volume percent of about 0.4%; and (g) is L-glutamic acid at a weight to volume percent of about 0.4%.

Embodiment N17

The composition of Embodiment N12, wherein (c) is L-aspartic acid at a weight to volume percent of about 2%; (e) is L-cysteine at a weight to volume percent of about 2%; and (g) is L-glutamic acid at a weight to volume percent of about 2%.

Embodiment N18

The composition of Embodiment N4 or N5, comprising (a), (b), (c), (d), (e), (f), (g), (h), (i), and (j).

Embodiment N19

The composition of Embodiment N4 or N5, comprising two of (a), (b), (c), (d), (e), (f), (g), (h), (i), and (j).

Embodiment N20

The composition of Embodiment N4 or N5, comprising three of (a), (b), (c), (d), (e), (f), (g), (h), (i), and (j).

Embodiment N21

The composition of Embodiment N4 or N5, comprising four of (a), (b), (c), (d), (e), (f), (g), (h), (i), and (j).

Embodiment N22

The composition of Embodiment N4 or N5, comprising five of (a), (b), (c), (d), (e), (f), (g), (h), (i), and (j).

Embodiment N23

The composition of Embodiment N4 or N5, comprising six of (a), (b), (c), (d), (e), (f), (g), (h), (i), and (j).

Embodiment N24

The composition of Embodiment N4 or N5, comprising seven of (a), (b), (c), (d), (e), (f), (g), (h), (i), and (j).

Embodiment N25

The composition of Embodiment N4 or N5, comprising eight of (a), (b), (c), (d), (e), (f), (g), (h), (i), and (j).

Embodiment N26

The composition of Embodiment N4 or N5, comprising nine of (a), (b), (c), (d), (e), (f), (g), (h), (i), and (j).

Embodiment N27

The composition of any one of Embodiments N1 to N26, wherein the composition is free of non-bonded tyrosine or a salt thereof.

Embodiment N28

The composition of any one of Embodiments N1 to N27, wherein the composition is free of non-bonded phenylalanine or a pharmaceutically acceptable salt thereof, at a weight percent from about 0.5% to about 4.0%.

Embodiment N29

The composition of any one of Embodiments N1 to N28, wherein the composition is free of non-bonded valine or a pharmaceutically acceptable salt thereof at a weight percent from about 0.5% to about 4.0%.

Embodiment N30

The composition of any one of Embodiments N1 to N29, wherein the composition is free of non-bonded arginine, or a pharmaceutically acceptable salt thereof, at a weight percent from about 0.5% to about 4.0%.

Embodiment N31

The composition of any one of Embodiments N1 to N30, wherein the composition is free of non-bonded methionine, or a pharmaceutically acceptable salt thereof, at a weight percent from about 0.5% to about 4.0%.

Embodiment N32

The composition of any one of Embodiments N1 to N31, wherein the composition is free of non-bonded serine, or a pharmaceutically acceptable salt thereof, at a weight percent from about 0.5% to about 4.0%.

Embodiment N33

The composition of any one of Embodiments N1 to N32, wherein the composition is free of non-bonded threonine, or a pharmaceutically acceptable salt thereof, at a weight percent from about 0.5% to about 4.0%.

Embodiment N34

The composition of any one of Embodiments N1 to N33, wherein the composition is free of non-bonded leucine, or a pharmaceutically acceptable salt thereof, at a weight percent from about 0.5% to about 4.0%.

Embodiment N35

The composition of any one of Embodiments N1 to N34, wherein the composition is free of non-bonded isoleucine, or a pharmaceutically acceptable salt thereof, at a weight percent from about 0.5% to about 4.0%.

Embodiment N36

The composition of any one of Embodiments N1 to N35, wherein the composition is free of non-bonded citrulline, or a pharmaceutically acceptable salt thereof, at a weight percent from about 0.5% to about 4.0%.

Embodiment N37

The composition of any one of Embodiments N1 to N36, wherein the composition is free of non-bonded alanine, or a pharmaceutically acceptable salt thereof, at a weight percent from about 0.5% to about 4.0%.

Embodiment N38

The composition of any one of Embodiments N1 to N37, wherein the composition is free of non-bonded asparagine, or a pharmaceutically acceptable salt thereof, at a weight percent from about 0.5% to about 4.0%.

Embodiment N39

The composition of any one of Embodiments N1 to N38, wherein the composition is free of non-bonded glycine, or a pharmaceutically acceptable salt thereof, at a weight percent from about 0.5% to about 4.0%.

Embodiment N40

The composition of any one of Embodiments N1 to N39, wherein the composition is free of non-bonded taurine, or a pharmaceutically acceptable salt thereof, at a weight percent from about 0.5% to about 4.0%.

Embodiment N41

The composition of any one of Embodiments N1 to N40, wherein the composition is free of non-bonded tryptophan, or a pharmaceutically acceptable salt thereof, at a weight percent from about 0.5% to about 4.0%.

Embodiment N42

The composition of any one of Embodiments N1 to N41, wherein the composition is free of non-bonded cystathione, or a pharmaceutically acceptable salt thereof, at a weight percent from about 0.5% to about 4.0%.

Embodiment N43

The composition of any one of Embodiments N1 to N42, wherein the composition is free of non-bonded 1-methylhistidine, or a pharmaceutically acceptable salt thereof, at a weight percent from about 0.5% to about 4.0%.

Embodiment N44

The composition of any one of Embodiments N1 to N43, wherein the composition is free of non-bonded 2 aminobutyric acid, or a pharmaceutically acceptable salt thereof, at a weight percent from about 0.5% to about 4.0%.

Embodiment N45

The composition of any one of Embodiments N1 to N44, wherein the composition is free of non-bonded glutamine, or a pharmaceutically acceptable salt thereof, at a weight percent from about 0.5% to about 4.0%.

Embodiment N46

The composition of any one of Embodiments N1 to N45, wherein the composition is free of non-bonded histidine, or a pharmaceutically acceptable salt thereof, at a weight percent from about 0.5% to about 4.0%.

Embodiment N47

The composition of any one of Embodiments N1 to N46, wherein the composition is free of non-bonded ornithine, or a pharmaceutically acceptable salt thereof, at a weight percent from about 0.5% to about 4.0%.

Embodiment N48

The composition of any one of Embodiments N1 to N47, wherein the composition is free of non-bonded lysine, or a pharmaceutically acceptable salt thereof, at a weight percent from about 0.5% to about 4.0%.

Embodiment N49

The composition of any one of Embodiments N1 to N48, wherein the composition is free of one or more of: non-bonded alanine or salt thereof, non-bonded arginine or a salt thereof, non-bonded asparagine or a salt thereof, non-bonded citrulline or a salt thereof, non-bonded glycine or a salt thereof, non-bonded isoleucine or a salt thereof, non-bonded leucine or a salt thereof, non-bonded lysine or a salt thereof, non-bonded methionine or a salt thereof, non-bonded 3-methylhistidine or a salt thereof, non-bonded phenylalanine or a salt thereof, non-bonded ornithine or a salt thereof, non-bonded proline or a salt thereof, non-bonded serine or a salt thereof, non-bonded taurine or a salt thereof, non-bonded threonine or a salt thereof, non-bonded tryptophan or a salt thereof, and non-bonded valine or a salt thereof.

Embodiment N50

A pharmaceutical composition comprising the composition of any one of Embodiments N1 to N49 and a pharmaceutically acceptable carrier.

Embodiment N51

The pharmaceutical composition of Embodiment N50, wherein the pharmaceutically acceptable carrier is sterile saline.

Embodiment N52

A method of disrupting a fungal biofilm, a bacterial biofilm, or a fungal biofilm and a bacterial biofilm, the method comprising contacting the biofilm with the composition of any of claims N1 to N49.

Embodiment N53

A method of disrupting a fungal biofilm, a bacterial biofilm, or a fungal biofilm and a bacterial biofilm, the method comprising contacting the biofilm with the pharmaceutical composition of claim N50 or N51.

Embodiment N54

A method of treating a fungal infection, preventing a fungal infection, treating formation of a fungal biofilm, preventing formation of a fungal biofilm, or a combination of two or more thereof in a subject in need, the method comprising administering to the subject the composition of any of claims N1 to N49.

Embodiment N55

A method of treating a fungal infection, preventing a fungal infection, treating formation of a fungal biofilm, preventing formation of a fungal biofilm, or a combination of two or more thereof in a subject in need, the method comprising administering to the subject the pharmaceutical composition of claim N50 or N51.

Embodiment N56

The method of any one of claims N52 to N55, comprising administering the composition or pharmaceutical composition intravenously, topically, via wound irrigation, intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment, transmucosally, or transdermally.

Embodiment N57

The method of any one of claims N54 to N56, wherein the infection comprises *Candida albicans, Candida guilliermondii, Candida parapsilosis, Candida glabrata, Candida tropicalis, Candida dubliniensis, Candida auris, Staphylococcus aureus, Escherichia coli, Pseudomonas aeruginosa, Staphylococcus epidermidis*, or a combination of two or more thereof.

Embodiment N58

The method of any one of claims N54 to N56, wherein the infection comprises *Candida albicans, Candida guilliermondii, Candida parapsilosis, Candida glabrata, Candida tropicalis, Candida dubliniensis, Candida* auris, or a combination of two or more thereof.

Embodiment N59

The method of any of claims N52 to N58, comprising topically administering the composition or pharmaceutical composition by irrigation.

Embodiment N60

The method of any of claim N52 or N53, wherein disrupting comprises contacting the composition or pharmaceutical composition with a biofilm in or on a catheter or in fluid communication with an animal or prior to attachment of the catheter for fluid communication in an animal.

Embodiment N61

A method of sterilizing an implant or biomedical device, optionally in fluid communication with a subject's circulatory system, the method comprising contacting a surface of the implant or a surface of the biomedical device with an effective amount of the composition of any one of claims N1 to N49.

Embodiment N62

A method of sterilizing an implant or biomedical device, optionally in fluid communication with a subject's circulatory system, the method comprising contacting a surface of the implant or a surface of the biomedical device with an effective amount of the pharmaceutical composition of claim N50 or N51.

Embodiment N63

The method of claim N61 or N62, wherein the biomedical device is a catheter or tube in fluid communication with the subject a subject's circulatory system.

Embodiment N64

A method of preventing formation of a biofilm, disrupting an existing biofilm on a surface, or a combination thereof, the method comprising contacting the surface with an effective amount of the composition of any one of claims N1 to N49.

Embodiment N65

A method of preventing formation of a biofilm, disrupting an existing biofilm on a surface, or a combination thereof, the method comprising contacting the surface with an effective amount of the pharmaceutical composition of claim N50 or N51.

Embodiment N66

The composition of any one of claims N1 to N49, further comprising glycerin.

Embodiment N67

The composition of any one of claims N1 to N49, further comprising glycerin at a weight to volume percentage of from about 0.1% to about 5.0%.

EXAMPLES

Example 1

Two types of biofilm assays were performed: a sustained inhibition assay and a disruption assay. The sustained inhibition assay assesses the compound's ability to prevent biofilm development throughout all stages of biofilm formation, while the disruption assay assesses the compound's ability to break up an existing mature biofilm. These assays are described in detail in the following article: Lohse, M. B., Gulati, M., Valle Arevalo, A., Fishburn, A., Johnson, A. D., and Nobile, C. J. (2017) Assessment and optimizations of *Candida albicans* in vitro biofilm assays. *Antimicrobial Agents and Chemotherapy* 61: e02749-16.

For fungal biofilm assays, all solutions were prepared in RPMI 1640 medium. All bacterial biofilm solutions were prepared in Trypic Soy Broth (TSB), supplemented with 1% glucose (henceforth referred to as TSB-G). All subsequent procedures were performed in a manner that maintained sterility. A solution of each amino acid to be tested was prepared in weight to volume concentrations ranging from 0.1-5.0%. Amino acids were also tested in combinations. Compound solutions were homogenized with gentle agitation in the dark (4° C., 24 hours) before use.

Thirty-four amino acids that occur freely in human blood were tested as follows: L-alanine, Beta-alanine, 2-aminoadipic acid, 2-aminobutyric acid, L-arginine, L-asparagine, L-aspartic acid, L-citrulline, L-cysteine, ethanolamine, L-glutamic acid, L-glycine, L-glutamine, L-histidine, 3-methyl-L-hi stidine, L-homocysteine L-isoleucine, L-leucine, L-lysine, L-methionine, L-ornithine, L-phenylalanine, O-phosphoethanolamine, L-proline, Trans-4-hydroxy-L-proline, L-serine, O-phospho-L-serine, L-taurine, L-threonine, L-tryptophan, L-tyrosine, and L-valine. Two amino acids (1-methyl-L-histidine and L-cystathionine) were prepared at a highest concentration of 0.2% due to their limited solubility. All biofilm assays were performed using 384-well non-tissue culture treated polystyrene plates. The fungal species tested are as follows: *Candida albicans, Candida guilliermondii, Candida parapsilosis, Candida glabrata, Candida tropicalis, Candida dubliniensis*, and *Candida auris*. The bacterial species tested are as follows: *Staphylococcus aureus* (standard wild type and methicillin-resistant strain USA300), *Escherichia coli, Pseudomonas aeruginosa* and *Staphylococcus epidermidis*.

Fungal strains were streaked on Yeast Peptone Dextrose (YPD) agar plates and incubated at 30° C. for 48 hours. A single colony from each strain to be tested was inoculated into YPD broth and grown for 12 hours, at 30° C., shaking at 225 rpm. For the fungal biofilm inhibition assay, 1 µl of saturated overnight cell culture was added to either 80 µL of RPMI-1640 or RPMI-1640 supplemented with the amino acid compound solution to be tested, in a 384-well plate. The cells were allowed to adhere to the plate for 90 minutes at 37° C. with shaking (350 rpm). Loosely bound cells were washed once with phosphate buffered saline (PBS) and 80 ul of RPMI-1640, or RPMI-1640 supplemented with the amino acid compound solution was added to the plate. The plate was further incubated for 24 hours at 37° C. with shaking (350 rpm). Media was carefully aspirated and the biofilm was measured by optical density at 600 nm. Twelve replicates were performed for each tested condition and the reported values are normalized to the control (RPMI-1640 media only). For the fungal biofilm disruption assays, 80 µL of RPMI-1640 was added to the plate, along with 1 µL of overnight cell culture. The cells were allowed to adhere to the plate for 90 minutes at 37° C. with shaking (350 rpm). Loosely bound cells were washed once with PBS and 80 µL of RPMI-1640 was added to the plate. The plate was further incubated for 24 hours at 37° C. with shaking (350 rpm). Media was carefully aspirated from the mature biofilm and 80 µL of RPMI-1640, or RPMI-1640 supplemented with the amino acid compound solution to be tested, was gently added to the plate. The plate was further incubated for 24 hours at 37° C. with shaking (350 rpm). Media was carefully aspirated and the biofilm was measured by optical density at 600 nm. Twelve replicates were performed for each tested condition and the reported values are normalized to the control (RPMI-1640 media only).

Bacterial strains were streaked on Blood Agar plates (5% sheep blood in Tryptic Soy Agar) and incubated at 37° C. for 24 hours. A single colony from each strain to be tested was inoculated in a TSB broth and grown for 12 hours, at 37° C. with shaking (225 rpm). For the bacterial biofilm inhibition assays, 1 µL of saturated overnight cell culture was added to either 80 µL of TSB-G, or TSB-G supplemented with the amino acid compound solution to be tested, in a 384-well plate. The cells were allowed to adhere to the plate for 60 minutes at 37° C. without shaking. The media was carefully aspirated and 80 µL of TSB-G, or TSB-G supplemented with the amino acid compound solution was added to the plate. The plate was further incubated for 24 hours at 37° C. without shaking. Media was carefully aspirated and the biofilm was measured by optical density at 600 nm. Eight or twelve replicates were performed for each tested condition and the reported values are normalized to the control (TSB-G media only). For the bacterial biofilm disruption assays, 80 µL of TSB-G was added to the plate, along with 1 µL of overnight cell culture. The cells were allowed to adhere to the plate for 60 minutes at 37° C. with no shaking. The media was carefully aspirated and 80 µL of TSB-G was added to the plate. The plate was further incubated for 24 hours at 37° C. with no shaking. Media was carefully aspirated from the mature biofilm and 80 µL of TSB-G, or TSB-G supplemented with the amino acid to be tested, was gently added to the plate. The plate was further incubated for 24 hours at 37° C. without shaking. Media was aspirated and the biofilm was measured by optical density at 600 nm. Twelve replicates were performed for each tested condition and the reported values are normalized to the control (TSB-G media only).

Results

Weight to volume concentrations ranging from 0.1-5.0% were tested for all amino acids individually and in combination. The solution found to best abolish both fungal and bacterial biofilms is: 0.5% Cysteine+0.5% Glutamic Acid+0.5% Aspartic Acid.

Although these three amino acid solutions individually have some anti-biofilm effects on fungal and bacterial biofilms on their own (biofilm formation is decreased on average by twofold for each), in combination, the effects are significantly increased (biofilm formation is decreased by tenfold). This tenfold decrease in biofilm formation, which is close to complete removal of the biofilm, indicates clear anti-biofilm synergy between these three amino acids when applied in combination.

At concentrations lower than 0.5% of each amino acid in combination, the biofilm inhibition and disruption rates are less effective. At concentrations above 0.5%, there is no increase in effectiveness against biofilms (see Table B for *C. albicans* data and Table C for *S. aureus* data). The same holds true for all species of microbes tested.

TABLE B

Biofilm Inhibition and Disruption Assays for *C. albicans*

| Condition | Biofilm Remaining (Inhibition) | Biofilm Remaining (Disruption) |
|---|---|---|
| RPMI Medium | 1 | 1 |
| 0.5% L-cysteine + 0.5% L-glutamic acid + 0.5% L-aspartic acid | 0.2 +/− 0.06 | 0.08 +/− 0.04 |
| 0.4% L-cysteine + 0.4% L-glutamic acid + 0.4% L-aspartic acid | 0.4 +/− 0.08 | 0.3 +/− 0.05 |
| 2% L-cysteine + 2% L-glutamic acid + 2% L-aspartic acid | 0.2 +/− 0.06 | 0.07 +/− 0.01 |

TABLE C

Biofilm Inhibition and Disruption Assays for *S. aureus*

| Condition | Biofilm Remaining (Inhibition) | Biofilm Remaining (Disruption) |
|---|---|---|
| TSB-G Medium | 1 | 1 |
| 0.5% L-cysteine + 0.5% L-glutamic acid + 0.5% L-aspartic acid | 0.02 +/− 0.008 | 0.4 +/− 0.09 |
| 0.4% L-cysteine + 0.4% L-glutamic acid + 0.4% L-aspartic acid | 0.3 +/− 0.05 | 0.5 +/− 0.04 |
| 2% L-cysteine + 2% L-glutamic acid + 2% L-aspartic acid | 0.2 +/− 0.09 | 0.3 +/− 0.06 |

Table D summarizes the results of the inhibition assay, which assesses each amino acid's ability to prevent biofilm development, promote biofilm growth, and neutral effects on bacteria (*S. aureus*) biofilm formation and fungal (*C. albicans*) biofilm formation at 1% amino acid concentrations (unless specifically noted); p<0.001.

Table E summarizes the results of the disruption assay, which assesses each amino acid's ability to break up (disrupt) an existing mature biofilm, promote biofilm growth, and neutral effects on bacteria (*S. aureus*) biofilm formation and fungal (*C. albicans*) biofilm formation at 1% amino acid concentrations (unless specifically noted); p<0.001.

For both Table D and Table E, a single dot [ie. ●] signifies minor effect (from about 10 to about 30% change), two dots [ie. ●●] signifies major effect (greater than about 30% change).

B Biofilm=Bacterial Biofilm

F Biofilm=Fungal Biofilm

Neutral=No effect on the biofilm

TABLE D

Results of Sustained Inhibition Biofilm Assay.

| | Reduce B Biofilm | Reduce F Biofilm | Promote B Biofilm | Promote F Biofilm | Reduce Both | Promotes Both | Neutral |
|---|---|---|---|---|---|---|---|
| Alanine | | | | | | | ● |
| Beta-Alanine | ● | | | | | | |
| 2 Aminoadipic Acid | ● | | | | | | |
| 2 Aminobutyric Acid | | | | | | | ● |
| Arginine | | | ● | | | | |
| Asparagine | | | ● | | | | |
| Aspartic Acid | ●● | ●● | | | ●● | | |
| Citrulline | | | ● | | | | |
| Cystathionine (0.2%) | | | | | | | ● |
| Cysteine | ●● | ●● | | | ●● | | |
| Ethanolamine | | ● | | | | | |
| Glutamine | | | | | | | ● |
| Glutamic Acid | ●● | ●● | | | ●● | | |
| Glycine | | | ● | | | | |
| Histidine | | | | | | | ● |
| Homocysteine (0.4%) | | ● | | | | | |
| Hydroxyproline | ● | | | | | | |
| Isoleucine | | | | | | | ● |
| Leucine | | | ● | | | | |
| Lysine | | | ● | | | | |
| Methionine | | | ● | | | | |
| 1-Methylhistidine | | | | | | | ● |
| 3-Methylhistidine | | | | ● | | | |
| Phenylalanine | | | ● | | | | |
| Ornithine | | | ● | | | | |
| Phosphoethanolamine | ● | | | | | | |
| Phosphoserine | | | | | | | ● |
| Proline | | | | | | | ● |
| Serine | | | ● | | | | |
| Taurine | | | ● | | | | |
| Threonine | | | ● | | | | |
| Tryptophan | | | | | | | ● |
| Tyrosine | | | | | | | ● |
| Valine | | | | ● | | | |

TABLE E

Results of Disruption Biofilm Assay.

| | Reduce B Biofilm | Reduce F Biofilm | Promote B Biofilm | Promote F Biofilm | Reduce Both | Promotes Both | Neutral |
|---|---|---|---|---|---|---|---|
| Alanine | | | ● | | | | |
| Beta-Alanine | | | | | | | ● |
| 2 Aminoadipic Acid | ● | | | | | | |
| 2 Aminobutyric Acid | | | | | | | ● |
| Arginine | | | ● | | | | |
| Asparagine | | | | | | | ● |
| Aspartic Acid | ●● | ●● | | | ●● | | |
| Citrulline | | | ● | | | | |
| Cystathionine (0.2%) | ● | | | | | | |
| Cysteine | ●● | ●● | | | ●● | | |
| Ethanolamine | | | | | | | ● |
| Glutamine | | | | | | | ● |
| Glutamic Acid | ●● | ●● | | | | | |
| Glycine | | | ● | | | | |

TABLE E-continued

Results of Disruption Biofilm Assay.

| | Reduce B Biofilm | Reduce F Biofilm | Promote B Biofilm | Promote F Biofilm | Reduce Both | Promotes Both | Neutral |
|---|---|---|---|---|---|---|---|
| Histidine | | | | | | | • |
| Homocysteine (0.4%) | | • | | | | | |
| Hydroxyproline | • | | | | | | |
| Isoleucine | | | • | | | | |
| Leucine | | | • | | | | |
| Lysine | | | • | | | | |
| Methionine | | | | | | | • |
| 1-Methylhistidine | | | | | | | • |
| 3-Methylhistidine | • | | | | | | |
| Phenylalanine | | | • | | | | |
| Ornithine | | | • | | | | |
| Phosphoethanolamine | • | | | | | | |
| Phosphoserine | • | • | | | | | |
| Proline | | • | • | | | | |
| Serine | | | • | | | | |
| Taurine | | | • | | | | |
| Threonine | | | | | | • | |
| Tryptophan | | | | | | | • |
| Tyrosine | | | | | | | • |
| Valine | • | | | | | | |

The following additional amino acids (in addition to L-cysteine, L-glutamic acid, and L-aspartic acid) also have anti-biofilm properties against fungal biofilms when administered individually in at least one of the two biofilm assays tested (sustained inhibition and/or disruption), but the effects are minimal (reduction by less than twofold): Ethanolamine; L-homocysteine; Phosphoserine; L-proline.

Unlike the optimal combination solution of 0.5% L-cysteine+0.5% L-glutamic acid+0.5% L-aspartic acid solution described above, when Ethanolamine, L-homocysteine, Phosphoserine, and L-proline are tested in combination at concentrations ranging from about 0.1 to about 5.0% weight to volume, there is no increase in effectiveness against biofilms (biofilm reduction remains at less than twofold).

The following additional amino acids (in addition to L-cysteine, L-glutamic acid, and L-aspartic acid) also have anti-biofilm properties against bacterial biofilms when administered individually at concentrations ranging from about 0.1 to about 5.0% weight to volume in at least one of the two biofilm assays tested (sustained inhibition and/or disruption), but the effects are minimal (reduction by less than twofold): Beta-alanine; 2-aminoadipic acid; Hydroxy-L-proline; O-phosphoethanolamine.

It was also discovered that certain amino acids support (improve) biofilm growth and therefore are not recommended to be administered to patients at risk of infection. The amino acids that support (improve) fungal biofilm growth in at least one of the two biofilm assays tested (sustained inhibition and/or disruption) are as follows: 3-methyl-L-histidine; L-valine.

The amino acids that support (improve) bacterial biofilm growth in at least one of the two biofilm assays tested (sustained inhibition and/or disruption) are as follows: L-alanine; L-arginine; L-asparagine; L-citrulline; L-glycine; L-isoleucine; L-leucine; L-lysine; L-methionine, L-phenylalanine; L-ornithine; L-proline; L-serine; L-taurine; L-threonine.

The following amino acids are neutral (i.e. they have no effects on bacterial or fungal biofilms) in both assays (sustained inhibition and disruption): 2-aminobutyric acid; L-glutamine; L-histidine; 1-methyl-histidine; L-tyrosine; L-tryptophan.

Example 2

Testing the optimal amino acid mixture solution that is effective against both fungal and bacterial biofilms (0.5% L-cysteine+0.5% L-glutamic acid+0.5% L-aspartic acid) in a microfluidic flow device biofilm model. This model mimics a human catheter biofilm infection. Microfluidic model will be performed using the experimental compositions detailed in Example 1.

The Microfluidic Assay allows for the visualization of biofilm formation at a single cell level when exposed to a fixed rate linear flow and is a derivate of the protocol Applicant previously described in the manuscript: Gulati, M., Ennis, C. L., Rodriguez, D. L., and Nobile, C. J. (2017) Visualization of biofilm formation in Candida albicans using an automated microfluidic device. JoVE 130: e56743, which is incorporated by reference in its entirety. This assay uses BioFlux 48-Well low-shear plates (Fluxion Biosciences), a BioFlux 1000Z (Fluxion Biosciences) microfluidic flow device, and a Zeiss AX10 microscope. Media is pre-warmed to the desired temperature (normally 37° C.) to avoid formation of bubbles during the experiment. The temperature controller of the system will be set to the desired temperature (normally 37° C.). Condensation will be removed from the interphase plate before setting up the experiment by running sterile air through the system at 2 dyne/cm2 for 10 minutes. The 48-well low shear plates (Fluxion Biosciences) will be placed in the holder and 600-1,000 µL of media and/or media and compound to test will be added to the inlet wells (volumes larger than 600 µL are needed for assays over 12 hours in length). The interphase plate will be positioned over the 48-well low shear plates (Fluxion Biosciences) and locked in place so that the system is airtight. Air will be removed from the flow wells by running the media from the inlet to outlet wells for 5 mins at 1 dyne/cm2. Overnight cultures will be grown in YPD at 30° C., the density determined in the morning, and cells will be diluted to a final density of OD600=0.5 (or equivalent to 1×107 cells) in 50 µL per well of the desired medium. It is recommended to have three replicates per strain or testing condition. Cells will be seeded into the flow cell chamber by adding the cell culture to the outlet well of the BioFlux 48-Well plate (Fluxion Biosciences) and running the system with a backward flow (from outlet to inlet) at 2 dyne/cm2 for 4 seconds. It is crucial to not exceed 4 seconds in order to prevent the cells from contaminating the inlet wells. The seeded cells will be allowed to adhere with no flow for 20 minutes at 37° C. Bright-field and phase contrast pre-wash images will be acquired from three different sections of the flow chamber in each well using a Zeiss AX10 microscope. Wells will be washed with media flowing from inlet to outlet wells at 1 dyne/cm2 for 5 minutes to remove non-adherent cells. The remaining cells will be incubated at 37° C. for 12 hours at 0.5 dyne/cm2. Bright-field and phase contrast images will be acquired from three different sections of the flow chamber in each well every 5 minutes using a Zeiss AX10 microscope for the remainder of the experiment. The percentage of area occupied by the biofilm will be quantified using the BioFlux Montage software (Fluxion Biosciences). The protocol is described in the following two manuscripts: (1) Gulati, M., Ennis, C. L., Rodriguez, D. L., and Nobile, C. J. (2017) Visualization of biofilm formation in *Candida albicans* using an automated microfluidic device. JoVE 130: e56743, which is incorporated by reference in its entirety, and (2) Lohse M B, Gulati M, Arevalo A V, Fishburn A, Johnson AD, Nobile C J; *Antimicrob Agents Chemother*. 2017 Mar. 13. pii: AAC.02749-16. doi: 10.1128/AAC.02749-16, which is incorporated by reference in its entirety.

Example 3

Testing the optimal amino acid mixture solution that is effective against both fungal and bacterial biofilms (0.5% L-cysteine+0.5% L-glutamic acid+0.5% L-aspartic acid) in a rat catheter model of biofilm infection. Methods to perform the assay are as follows:

Animals: Specific-pathogen-free male Sprague-Dawley rats weighing 350 g (Harlan)

Medications: (1) Heparin sodium for injection 1000 USP unitis/mL (APP Pharmaceuticals); (2) Xylazine (Sigma-Aldrich); (3) Buprenorphine 0.3 mg/mL (Hospital Pharmacy); (4) Ketamine HCl 500 mg/10 mL (Bedford Laboratories); (5) Double Antibiotic Ointment:Bacitracin Zinc and Polymyxin B Sulfate (Fougera).

Surgical materials: (1) Polyethylene tubing with inner diameter 1.14 mm and outer diameter 1.57 mm. (PE 160, Intramedic, Becton Dickinson); (2) Three way large bore stopcock with rotating male luer lock adapter (Baxter Healthcare Corporation); (3) Rodent jacket, rat 250-350 g (Braintree Scientific, Inc); (4) Tether, 18' sewn (Braintree Scientific, Inc); (5) Scrub Care Surgical Scrub Brush-Sponge/Nail Cleaner (catalog Cardinal Health); (6) Polysulfone Button Tether for rats, 0.090 in lumen, 12 in (30 cm) (sterile) (Instech Solomon); (7) Skin stapler 5.7 mm×3.9 mm (Ethicon Endo-Surgery); (8) Surgical suture, sterile, non absorbable, Silk black braided 2-0 18" (3.0 metric, 45 cm) (Ethicon Inc); (9) Surgical dissecting microscope (Stereo Zoom Microscope with fiber optic illuminator control (PZ-MIII-BS) World Precision Instruments); (10) Sterile syringes (variety of volumes); (11) Surgical attire: sterile surgical gloves, sterile gown, and surgical mask; (12) Rodent hair clipper (A5 power pro clipper, Oster) 13. Rat dissecting kit (World Precision Instruments); (13) Far Infared warming pad 14"×14" (Kent Scientific Corporation)

Fungal Isolates and Media

Media 1: YPD medium supplemented with uridine: 1% yeast extract, 2% bacto peptone, 2% glucose, and uridine 80 µg/mL Materials for Evaluation of Selected Endpoints Microbiologic counts (optional): (1) Sonicating water bath (FS 14 with 40-kHz transducer, Fisher Scientific); (2) Sabouraud dextrose agar (SDA plates: 4% dextrose, 1% peptone 1.5% agar, pH 5.6; (3) Tissue homogenizer (Polytron 3100, Brinkman Instruments)

Confocal or fluorescent microscopy (optional): (1) Fluorescent probes; (2) Calcofluor white or Fluorescent brightener 28 (Sigma-Aldrich): (3) FUN1 live dead yeast stain (Molecular Probes, Invitrogen); (4) Concavalin A Alexa Fluor 488 (Molecular Probes, Invitrogen); (5) Glass-bottom petri dish (coverslip 1.5, 35-mm disk P325G 1.5-14C, MatTek); (6) Confocal or fluorescent microscope with inverted objective (such as Zeiss Axiovert 200).

Scanning electron microscopy (optional): (1) Glutaraldehyde (25%) (Sigma-Aldrich); (2) Formaldehyde (37%) (Sigma-Aldrich); (3) Phosphate-buffered saline (PBS) (0.15 M NaCl, pH 7.4); (4) Osmium tetroxide (Electron Microscopy Sciences); (5) Critical point drier (Tousimis); (6) Gold sputter coater (Auto Conductavac IV, Seevac Inc.); (7) Ultra smooth carbon adhesive tabs (12 mm, Electron Microscopy Sciences); (8) Aluminum mounts (12.7 mm, Electron Microscopy Sciences); (9) Scanning electron microscope (JSM-6100, JEOL)

*Candida* biofilm cell nucleic acid collection (optional): (1) AE buffer (50 mM sodium acetate pH 5.2, 10 mM EDTA); (2) Liquid nitrogen; (3) Reagents for hot phenol RNA extraction METHODS Preparation of catheters: (1) Cut polyethylene tubing into 50 cm in length. This catheter length is calculated based on placement in the jugular vein 2 cm above the right atrium, subcutaneous tunneling, and extension though an external protective device to the top of the animal cage where it will be secured for access. The volume of this catheter length is approximately 500 µL. With luer stub and stop cock, the total catheter volume is approximately 700 µL. (2) Sterilize catheters by ethylene oxide gas sterilization as autoclaving may destroy them.

Preparation of surgical equipment: (1) Sterilize surgical equipment, including surgical gowns, drapes, tethers, and surgical tools by autoclave. (2) Use prepackaged, sterilized stopcocks with luer stubs, sutures, and surgical gloves.

Catheter placement: (1) Anesthetize animals by intraperitoneal injection of a mixture of ketamine (80 mg/kg) and xylazine (8 mg/kg). This anesthesia protocol should produce anesthesia for approximately 120 min. (2) Prepare the animal for the surgical procedure by removing hair from the midscapular space, anterior chest, and neck with a rodent clipper. Prepare skin area with an antiseptic surgical scrub brush. (3) Create a sterile field under the surgical microscope by placing the rat in the supine position and preparing the surgical area with sterile drapes. Wear sterile gloves, mask, and gown. (4) Make a vertical incision in skin of the anterior neck just right of midline and use blunt surgical dissection to expose the right jugular vein. (5) To subcutaneously tunnel the catheter, create a second incision at the scruff and use blunt surgical dissection toward the initial surgical incision. Next, tunnel the proximal end of the catheter through this subcutaneous space to the midscapular space and externalize the catheter at the site of the second surgical incision. (6) Stabilize the jugular vein and make a longitudinal incision of a few millimeters to the vein wall using the vannas scissors. Instill heparinized saline (100 units/ml) into the catheter and insert the catheter in the vein (superior vena cava) opening. Advance to a site above the right atrium (approximately 2 cm). If the catheter is appropriately placed, blood should be able to be easily withdrawn. Conversely, if the catheter is in the atrium, it may be difficult to withdraw blood. Secure the catheter to the vein with (2-0) silk ties. (7) Secure the catheter to the subscapular skin scruff via a button using surgical staples Close both incisions with surgical staples and apply antibiotic ointment. Position a tether and rodent jacket on the animal to protect the catheter Secure the distal catheter segment and stopcock above the cage to allow easy access to catheter. (8) Surgical placement of a rat jugular venous catheter. (A) The catheter is inserted and secured in the jugular vein of an anesthetized animal. (B) The wire casing and rodent jacket protect the catheter and prevent the animal from disrupting the catheter. (9) Monitor the animal and wrap in a warming pad until it can lift its head and remain sternal. (10) Administer narcotic analgesia with buprenorphine 0.05 mg/kg subcutaneously twice daily for 24 h. (11) Allow the catheter to remain in place for 24 h prior to infection to allow for catheter surface conditioning with host proteins.

Animal and catheter maintenance: (1) Monitor the animals for signs of distress every 8 h through the study. In necessary, consider additional administration of buprenorphine 0.05 mg/kg subcutaneously twice daily for analgesia. (2) The anterior neck incision and the catheter exit site should be examined daily for signs of inflammation or purulence. In our experience with this protocol, superficial infections are uncommon. (3) House animals in an environmentally controlled room with 12-h light-dark cycle and maintain on a standard ad libitum rat diet. Following surgery and for the duration of the experiments, house animals singly in shoe box cages with normal bedding.

Preparation of inoculum: (1) Store fungal strains in 15% (vol/vol) glycerol stock at −80° C. Prior to experiments, maintain strains on YPD medium supplemented with uridine. *C. albicans, C. glabrata*, and *C. parapsilosis* have successfully produced biofilms in this model. (2) Grow strains in YPD medium supplemented with uridine at 30° C. on an orbital shaker set to 200 RPM. Harvest during late logarithmic phase (this time period can vary among strains thus should be determined experimentally). Enumerate the cells by means of hemocytometer count. Adjust the final density to $1\times10^6$ cells/mL in YPD supplemented with uridine.

Infection of catheter: (1) Instill 700 µL of fungal inoculum in the catheter using a sterile syringe and the stopcock. This volume should fill the catheter lumen. (2) Allow the inoculum to dwell for 6 h, then withdraw or flush the catheter volume. Lock the catheter with same volume of sterile heparinized saline (heparin 100 units/mL, 0.15M NaCl).

Lock treatment of catheter (optional): (1) Prepare antifungal drugs or other agents to be tested in sterile saline (0.15M NaCl). (2) After 24 h of biofilm growth, withdraw or flush the heparinized saline from the catheter. (3) Instill the drug (700 µL) in the catheter with a sterile syringe and lock in place).

Harvesting the catheter: (1) Sacrifice animals by $CO_2$ asphyxiation. Typical collection times are 24 h after infection or 24 h after treatment administration. (2) Aseptically remove the catheter from the animal. Collect the proximal catheter segment (approximately 8 cm). (3) Gently place the proximal catheter tip (that was inserted in the animal) on sterile gauze. Allow the catheter fluid to drain the length of the catheter by capillary action. (4) Collect the proximal segment of catheter that was inserted in to the animal (approximately 2 cm in length). This segment can be prepared for microbiological enumeration, microscopy, or nucleic acid collection.

Endpoint Determination

Microbiological counts (optional): (1) Place the catheter section in 1 mL sterile saline. (2) Sonicate sample for 10 min and vigorously vortex for 30 seconds. (3) To ascertain the extent of disease dissemination, remove the kidneys or other internal organs from the animal. Place in a suitable volume of saline and homogenize. (4) Plate serial dilutions (1:10) of the catheter fluid and organ material on SDA plates and incubate for 24 h at 30° C. (5) Enumerate fungal colony counts as an estimate of fungal viable burden per organ.

Fluorescent or confocal microscopy (optional): (1) Cut the catheter segment perpendicular to the catheter length with an 11-blade scalpel into multiple 2- to 3-mm-long "doughnut" segments. (2) Stain the catheter segments with fluorescent probes (FUN1 50 µM, Concanavalin Alexa Fluor 488 conjugate 200 mM, or calcofluor white (22.5 µg/ml) at 30° C. for 30 min in the dark. (3) Place catheter segments on the coverslip of a glass-bottom petri dish with the cut edge against the coverslip. Image the luminal surface of the catheter by fluorescent or confocal microscopy using the light source and filters appropriate for selected dyes.

Scanning electron microscopy (optional): (1) Cut the catheter segment perpendicular to the catheter length with an 11-blade scalpel into multiple 2- to 3-mm-long "doughnut" segments. (2) Place segments in fixative (1% glutaraldehyde, 4% formaldehyde in PBS) for 16 hours at 4° C. (3) Gently remove fixative and add 1 mL PBS for 10 min to wash samples. (4) Place samples in osmium tetroxide (1% in PBS) for 30 min. Osmium tetroxide is toxic and should only be used in a hood with protective gloves, lab coat, and eye wear. Proper disposal is required. (5) Gently remove osmium tetroxide and add 1 mL PBS for 10 min to wash samples. (6) Dehydrate samples by treating samples to a series of ethanol washes (30% for 10 min, 50% for 10 min, 70% for 10 min, 95% for 10 min, and 100% for 10 min). (7) Use critical point drying according to instruction to accomplish final desiccation. Our protocol uses three 10 minute $CO_2$ soaks prior to achieving critical point. (8) Section catheter segments length wise and mount the specimens on aluminum stubs with the luminal side visible. (9) Coat samples with gold appropriate for scanning electron microscope using a sputter coater. Our protocol coats samples for 2.5 to 3 minutes. (10) Image the luminal surface of catheter samples using scanning electron microscopy Example 4

Testing the optimal amino acid mixture solution that is effective against both fungal and bacterial biofilms (0.5% L-cysteine+0.5% L-glutamic acid+0.5% L-aspartic acid) in combination with known antimicrobial agents (antifungals for fungal biofilms and antibiotics for bacterial biofilms) to determine if there are synergistic effects with known antimicrobial therapeutics. Current antifungal and antibiotics are largely ineffective against biofilms.

We will test the experimental composition with one or a plurality of antibiotics and/or antifungals disclosed above to identify whether the antibiotics and/or antifungals will have a synergistic effect on biofilm inhibition and/or disruption in combination with the experimental composition. Known therapeutic doses of antibiotics and/or antifungals will be used in combination with one or plurality of ranges of experimental compositions. A non-limiting experimental protocol is as follows:

Anti-fungal Compositions Tested. (1) Experimental Composition: (0.5% L-cysteine+0.5% L-glutamic acid+0.5% L-aspartic acid); (2) Experimental Composition: (0.5%

L-cysteine+0.5% L-glutamic acid+0.5% L-aspartic acid) Plus Ketoconazole; (3) Experimental Composition: (0.5% L-cysteine+0.5% L-glutamic acid+0.5% L-aspartic acid) Plus Fluconazole; (4) Experimental Composition: (0.5% L-cysteine+0.5% L-glutamic acid+0.5% L-aspartic acid) Plus Caspofungin; (5) Experimental Composition: (0.5% L-cysteine+0.5% L-glutamic acid+0.5% L-aspartic acid) Plus Amphotericin-B; (6) Negative Control (not including Experimental Composition)

Anti-bacterial Compositions Tested. (1) Experimental Composition: (0.5% L-cysteine+0.5% L-glutamic acid+ 0.5% L-aspartic acid); (2) Experimental Composition: (0.5% L-cysteine+0.5% L-glutamic acid+0.5% L-aspartic acid) Plus Ampicllin; (3) Experimental Composition: (0.5% L-cysteine+0.5% L-glutamic acid+0.5% L-aspartic acid) Plus Tetracycline; (4) Experimental Composition: (0.5% L-cysteine+0.5% L-glutamic acid+0.5% L-aspartic acid) Plus Vancomycin; (5) Experimental Composition: (0.5% L-cysteine+0.5% L-glutamic acid+0.5% L-aspartic acid) Plus Cephalosporin; (6) Negative Control (not including Experimental Composition).

Disruption Assay (Treatment):96-well plates will be inoculated with *Candida albicans* or *Staphylococcus aureus* at the concentrations disclosed in Example 1, and biofilms will be allowed to form and each composition will be tested for effectively disrupting the biofilm by measuring absorbance at O.D. 600 nm.

Inhibition Assay (Prophylaxis): 96-well plates will be inoculated with *Candida albicans* or *Staphylococcus aureus* at the concentrations disclosed in Example 1 in combination with each of the composition listed above, and each composition will be tested for effectively preventing the formation of the biofilm by measuring absorbance at O.D. 600 nm.

It is expected that administration of the experimental composition before, contemporaneously with, or after the one or plurality of antibiotics and/or antifungals will lead to a synergistic effect at disrupting and/or inhibiting bacterial and/or fungal biofilms.

Lohse M B, Gulati M, Arevalo A V, Fishburn A, Johnson A D, Nobile C J; *Antimicrob Agents Chemother.* 2017 Mar. 13. pii: AAC.02749-16. doi:10.1128/AAC.02749-16, which is incorporated by reference in its entirety.

Example 5

Testing the optimal amino acid mixture solution that is effective against both fungal and bacterial biofilms (0.5% L-cysteine+0.5% L-glutamic acid+0.5% L-aspartic acid) as a sterilization agent for implants and other medical devices.

An implant model will be used for determining whether the non-bonded amino acids of the disclosure are useful for sterilizing medical device equipment. A protocol for this assay is as follows:

Squares of silicone (1.5 cm by 1.5 cm) will be cut from silicone sheets (Cardiovascular Instrument Corp.), washed in water, and autoclaved. Prior to inoculation, the squares will be incubated with bovine serum (B-9433; Sigma) overnight and then washed once in phosphate-buffered saline (PBS) immediately before inoculation. Strains will grown overnight in yeast extractpeptone-dextrose at 37° C. and diluted in SD medium plus 50 mM glucose to an optical density at 600 nm (OD600) of 1.0 or in Spider medium to an OD600 of 0.5.

Inoculation will be accomplished by adding 2 ml of this cell suspension to a silicone square in a 12-well plate and incubating at 37° C. for 90 min with gentle agitation (at 150 rpm). After this adherence step, each square will be washed with PBS and 2 ml of fresh medium containing the experimental composition will be added. Biofilms will be grown for 24 hours at 37° C. with gentle agitation in the presence and absence of the composition.

Biofilm growth disruption and/or inhibition will be assessed by confocal scanning laser microscopy as described in Nobile, C. J., Fox, E. P, Nett, J. E., Sorrells, T. R., Mitrovich, Q. M., Hernday, A. D., Tuch, B. B., Andes, D. R., and Johnson, A. D. (2012) A recently evolved transcriptional network controls biofilm development in *Candida albicans*. Cell 148: 126-138, which is incorporated by reference in its entirety.

What is claimed is:

1. A pharmaceutical composition comprising about 0.5% w/v of L-cysteine, about 0.5% w/v of L-glutamic acid, about 0.5% w/v of L-aspartic acid, and sterile saline.

2. A method of disrupting a fungal biofilm, a bacterial biofilm, or a fungal biofilm and a bacterial biofilm, the method comprising contacting the biofilm with the pharmaceutical composition of claim 1.

3. A method of treating a fungal infection, preventing a fungal infection, treating formation of a fungal biofilm, preventing formation of a fungal biofilm, or a combination of two or more thereof in a subject in need, the method comprising administering to the subject the pharmaceutical composition of claim 1.

4. The method of claim 3, wherein the infection comprises *Candida albicans, Candida guilliermondii, Candida parapsilosis, Candida glabrata, Candida tropicalis, Candida dubliniensis, Candida auris*, or a combination of two or more thereof.

5. A method of sterilizing an implant or biomedical device, optionally in fluid communication with a subject's circulatory system, the method comprising contacting a surface of the implant or a surface of the biomedical device with an effective amount of the pharmaceutical composition of claim 1.

6. A method of preventing formation of a biofilm, disrupting an existing biofilm on a surface, or a combination thereof, the method comprising contacting the surface with an effective amount of the pharmaceutical composition of claim 1.

7. The pharmaceutical composition of claim 1, further comprising glycerin.

8. The pharmaceutical composition of claim 7, comprising glycerin at a weight to volume percentage of from about 0.1% to about 5.0%.

9. A pharmaceutical composition comprising about 0.4% w/v of L-cysteine, about 0.4% w/v of L-glutamic acid, about 0.4% w/v of L-aspartic acid, and sterile saline.

10. A method of disrupting a fungal biofilm, a bacterial biofilm, or a fungal biofilm and a bacterial biofilm, the method comprising contacting the biofilm with the pharmaceutical composition of claim 9.

11. A method of treating a fungal infection, preventing a fungal infection, treating formation of a fungal biofilm, preventing formation of a fungal biofilm, or a combination of two or more thereof in a subject in need, the method comprising administering to the subject the pharmaceutical composition of claim 9.

12. The method of claim 11, wherein the infection comprises *Candida albicans, Candida guilliermondii, Candida parapsilosis, Candida glabrata, Candida tropicalis, Candida dubliniensis, Candida auris*, or a combination of two or more thereof.

13. A method of sterilizing an implant or biomedical device, optionally in fluid communication with a subject's circulatory system, the method comprising contacting a surface of the implant or a surface of the biomedical device with an effective amount of the pharmaceutical composition of claim 9.

14. A method of preventing formation of a biofilm, disrupting an existing biofilm on a surface, or a combination thereof, the method comprising contacting the surface with an effective amount of the pharmaceutical composition of claim 9.

15. The pharmaceutical composition of claim 9, further comprising glycerin.

16. The method of claim 2 for disrupting the fungal biofilm.

17. The method of claim 10 for disrupting the fungal biofilm.

18. The method of claim 6, wherein the biofilm is a fungal biofilm.

19. The method of claim 14, wherein the biofilm is a fungal biofilm.

20. A pharmaceutical composition comprising about 0.2% w/v of L-cysteine, about 0.2% w/v of L-glutamic acid, about 0.2% w/v of L-aspartic acid, and sterile saline.

* * * * *